United States Patent
Villegas et al.

(10) Patent No.: US 7,427,487 B2
(45) Date of Patent: Sep. 23, 2008

(54) CONSTITUTIVELY ACTIVE CXCR3 G PROTEIN-COUPLED CHEMOKINE RECEPTOR AND MODULATORS THEREOF FOR THE TREATMENT OF INFLAMMATORY DISORDERS

(75) Inventors: Sonia Villegas, San Diego, CA (US); Chen W. Liaw, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/548,898

(22) PCT Filed: Mar. 15, 2004

(86) PCT No.: PCT/US2004/007930

§ 371 (c)(1),
(2), (4) Date: Jun. 28, 2006

(87) PCT Pub. No.: WO2004/083394

PCT Pub. Date: Sep. 30, 2004

(65) Prior Publication Data

US 2007/0160987 A1    Jul. 12, 2007

Related U.S. Application Data

(60) Provisional application No. 60/455,911, filed on Mar. 18, 2003.

(51) Int. Cl.
| | |
|---|---|
| C07K 14/705 | (2006.01) |
| C12N 15/12 | (2006.01) |
| C12N 15/62 | (2006.01) |
| G01N 33/566 | (2006.01) |

(52) U.S. Cl. .................. 435/7.2; 435/7.21; 435/69.1; 435/69.7; 435/252.3; 435/320.1; 530/350; 536/23.4; 536/23.5

(58) Field of Classification Search .................. None
See application file for complete search history.

(56) References Cited

U.S. PATENT DOCUMENTS

| | | |
|---|---|---|
| 6,184,358 B1 | 2/2001 | Loetscher et al. |
| 6,555,339 B1 * | 4/2003 | Liaw et al. .......... 435/69.1 |
| 2003/0018182 A1 | 1/2003 | Behan et al. |

OTHER PUBLICATIONS

Rasmussen et al., Mutation of a Highly Conserved Asparatic Acid in the beta2 Adrenergic Receptor: Constitutive Activation, Structural Instability, and Conformational Rearrangement of Transmembrane Segment 6, Feb. 1999, Mol. Pharmoc. 56:175-184.*

* cited by examiner

*Primary Examiner*—John D Ulm
(74) *Attorney, Agent, or Firm*—James S. Keddie; Carol L. Francis; Bozicevic, Field & Francis LLP

(57) ABSTRACT

The invention disclosed in this patent document relates to transmembrane receptors, particularly to a human G protein-coupled receptor, more particularly to a CXC chemokine receptor subtype 3 (CXCR3), and most particularly to mutated (non-endogenous) version of the human CXCR3 for evidence of constitutive activity and uses thereof. In some embodiments the altered versions of CXCR3 are used, inter alia, for the direct identification of candidate compounds such as receptor agonists, inverse agonists, partial agonist or antagonist for use in, for example and not limitation, graft rejection; inflammatory skin disease; inflammatory bowel disease; allergic inflammation, allergic pulmonary inflammation, inflammatory demyelinating neuropathy, CNS inflammation; rheumatoid arthritis, bronchiolitis obliterans syndrome, periodontal disease and neurodegenerative disease.

21 Claims, 5 Drawing Sheets

CONSTITUTIVELY ACTIVE CXCR3 G PROTEIN-COUPLED CHEMOKINE RECEPTOR AND MODULATORS THEREOF FOR THE TREATMENT OF INFLAMMATORY DISORDERS

FIELD OF THE INVENTION

The invention disclosed in this patent document relates to transmembrane receptors, and more particularly to a G protein-coupled receptor ("GPCR") for which the endogenous ligand has been identified; and specifically to a CXC chemokine receptor subtype-3 ("CXCR3") that has been altered to establish constitutive activity of the receptor. In some embodiments the altered versions of CXCR3 are used, inter alia, for the direct identification of candidate compounds such as receptor agonists, inverse agonists, partial agonist or antagonist for use in, for example and not limitation, graft rejection; inflammatory skin disease; inflammatory bowel disease; allergic inflammation, allergic pulmonary inflammation, inflammatory demyelinating neuropathy, CNS inflammation; rheumatoid arthritis, bronchiolitis obliterans syndrome, periodontal disease and neurodegenerative disease. Candidate compounds identified according to the methods disclosed herein may be useful in primates, including but not limited to, humans and non-human primates; as well other mammals, including but not limited to, dogs, cats, rats, mice, horses, sheep, pigs, and cows.

BACKGROUND OF THE INVENTION

A. G Protein-Coupled Receptors

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs. Receptors, including GPCRs, for which the endogenous ligand has been identified are referred to as "known" receptors, while receptors for which the endogenous ligand has not been identified are referred to as "orphan" receptors.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

Generally, when an endogenous ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., 43 *Life Sciences* 1095 (1988). Although other G proteins exist, currently, $G_q$, $G_s$, $G_i$, $G_z$ and $G_o$ are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to any theory, it is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

B. CXC Chemokine Receptor Subtype-3 ("CXCR3")

The CXC chemokine receptor subtype 3 (CXCR3) was cloned and originally referred to as GPR9 in 1995 and mapped incorrectly to human chromosome 8p11.2-12 (Marchese et al., 23, 609-618 (1995)) but was later mapped correctly to Xq13 (Loetscher et al., Eur J Immunol 28: 3696-3705 (1998)). After much analysis of GPR9, this receptor was identified to bind to one or more members of the chemokine superfamily of chemotatic cytokines and received its new nomenclature as CXCR3. CXCR3 was identified to bind to three agonists, γ-interferon inducible protein-10 ("IP-10"), interferon inducible T cell α-chemoattractant ("I-TAC"), and monoline induced by γ-inteferon ("Mig"). Murphy, P. M., et al., Pharmacol Rev 2000 March;52(1): 145-76.

CXCR3 has been determined to be expressed in circulating blood T-cells, B-cells, natural killer (NK) cells, and eosinophils. An increase in the expression levels and responsiveness of the CXCR3 is detected when T cells are active. This obser-

| | | |
|---|---|---|
| Claritin ® (allergies) | Prozac ® (depression) | Vasotec ® (hypertension) |
| Paxil ® (depression) | Zoloft ® (depression) | Zyprexa ® (psychotic disorder) |
| Cozaar ® (hypertension) | Imitrex ® (migraine) | Zantac ® (reflux) |
| Propulsid ® (reflux disease) | Risperdal ® (schizophrenia) | Serevent ® (asthma) |
| Pepcid ® (reflux) | Gaster ® (ulcers) | Atrovent ® (bronchospasm) |
| Effexor ® (depression) | Depakote ® (epilepsy) | Cardura ® (prostatic ypertrophy) |
| Allegra ® (allergies) | Lupron ® (prostate cancer) | Zoladex ® (prostate cancer) |
| Diprivan ® (anesthesia) | BuSpar ® (anxiety) | Ventolin ® (bronchospasm) |
| Hytrin ® (hypertension) | Wellbutrin ® (depression) | Zyrtec ® (rhinitis) |
| Plavix ® (MI/stroke) | Toprol-XL ® (hypertension) | Tenormin ® (angina) |
| Xalatan ® (glaucoma) | Singulair ® (asthma) | Diovan ® (hypertension) |
| Harnal ® (prostatic hyperplasia) | | |
| (Med Ad News 1999 Data). | | | vation revealed that CXCR3 is involved in inflammation, as well as, leukocyte trafficking and immune surveillance.

SUMMARY OF THE INVENTION

The present invention discloses nucleic acid molecules and the proteins for a non-endogenous, constitutively activated version of human CXCR3 receptor, referred to herein as, N134S. The N134S receptor has been determined to be a constitutively active form of the human CXCR3 created by a point mutation from an asparagine amino acid residue located at position 134 to a serine residue.

The present invention relates to non-endogenous, constitutively activated versions of the human CXCR3 receptor and various uses of such receptor. In some embodiments, CXCR3 has an amino acid sequence of SEQ. ID. NO: 6. In some embodiments, CXCR3 is encoded by a nucleotide sequence of SEQ ID NO: 5.

In further aspects the present invention is directed to plasmids comprising a vector and a cDNA having SEQ. ID. NO: 5.

In some aspects the present invention is directed to host cells comprising a plasmid wherein the plasmid comprises a vector and a cDNA having SEQ. ID. NO: 5.

In additional aspects the present invention is directed to methods for directly identifying a non-endogenous candidate compound as an agonist, an inverse agonist, partial agonist or an antagonist to an endogenous CXCR3. The methods comprise the steps of: (a) subjecting the endogenous CXCR3 to constitutive receptor activation to create a non-endogenous, constitutively activated CXCR3; (b) contacting the non-endogenous candidate compound with the non-endogenous, constitutively activated CXCR3; and (c) identifying the non-endogenous candidate compound as an agonist, an inverse agonist, a partial agonist or an antagonist to the constitutively activated CXCR3 by measuring a difference in an intracellular-signal induced by the contacted compound as compared with an intracellular signal in the absence of the contacted compound. These identified candidate compounds can then be utilized in pharmaceutical composition(s) for treatment of disease and disorders relating to the CXCR3 receptor, including but not limited to, graft rejection; inflammatory ski disease; inflammatory bowel disease; allergic inflammation, allergic pulmonary inflammation, inflammatory demyelinating neuropathy, CNS inflammation; rheumatoid arthritis, bronchiolitis obliterans syndrome, periodontal disease and neurodegenerative disease.

In additional aspects the present invention is directed to the preparation of a medicament for the prevention or treatment of a CXCR3 related disorder such as graft rejection selected from the group consisting of heart, lung, kidney and skin graft, and wherein the graft is an allograft or a xenograft.

In additional aspects the present invention is directed to the preparation of a medicament for the prevention or treatment of a CXCR3 related disorder such as an inflammatory disorder selected from the group consisting of inflammatory skin disease, inflammatory bowel disease, allergic inflammation, allergic pulmonary inflammation, inflammatory demyelinating neuropathy, CNS inflammation, rheumatoid arthritis, bronchiolitis obliterans syndrome, periodontal disease and neurodegenerative disease.

In additional aspects the present invention is directed to the preparation of a medicament for the prevention or treatment of a CXCR3 related disorder such as an inflammatory skin disease selected from the group consisting of psoriasis, lichen planus, chronic discoid lupus erthematosus, allergic patch test reactions, and Jessner's lymphocytic infiltration of the skin.

In additional aspects the present invention is directed to the preparation of a medicament for the prevention or treatment of a CXCR3 related disorder such as CNS inflammation selected from the group consisting of multiple sclerosis, focal stroke and encephalomyelitis.

In additional aspects the present invention is directed to compounds identified by the methods set forth above and described below.

In additional aspects the present invention is directed to compositions, including pharmaceutical compositions, comprising compounds directly identified by the methods of the present invention.

In some aspects the present invention is directed to methods of modulating a physiological process comprising. subjecting an endogenous CXCR3 to constitutive receptor activation to create a non-endogenous, constitutively activated CXCR3. The physiological process is thereby modulated. In some embodiments, the endogenous CXCR3 has an amino acid sequence of SEQ ID NO: 6.

In some embodiments the physiological process is selected from the group consisting of leukocyte trafficking, immune surveillance, innate and adaptive immune responses and various forms of pathological inflammation.

In additional aspects, the present invention is directed to methods of modulating a physiological process comprising: (a) subjecting an endogenous CXCR3 to constitutive receptor activation to create a non-endogenous constitutively activated CXCR3; and (b) contacting the non-endogenous, constitutively activated CXCR3 with a non-endogenous agonist, inverse agonist, partial agonist or antagonist of said CXCR3. The physiological process is thereby modulated. In some embodiments, the endogenous CXCR3 has an amino acid sequence of SEQ ID NO: 6. In some embodiments the physiological process is selected from the group consisting of leukocyte trafficking, immune surveillance, innate and adaptive immune responses and various forms of pathological inflammation.

In some aspects the present invention is directed to methods for directly identifying a non-endogenous candidate compound as a compound having activity selected from the group consisting of inverse agonist activity and agonist activity, to an endogenous, constitutively active G protein coupled cell surface receptor (GPCR) comprising the steps of: (a) contacting a non-endogenous candidate compound with a GPCR Fusion Protein, the GPCR Fusion Protein comprising the endogenous, constitutively active CXCR3 and a G protein; and (b) identifying the non-endogenous candidate compound as an agonist, an inverse agonist, partial agonist or antagonist to the endogenous constitutively activated CXCR3 by measuring a difference in an intracellular signal induced by the contacted compound as compared with an intracellular signal in the absence of the contacted compound.

In additional aspects the present invention is directed to methods for directly identifying a non-endogenous candidate compound as a compound having activity selected from the group consisting of inverse agonist activity and agonist activity, to an endogenous, constitutively active G protein coupled cell surface receptor (GPCR) comprising the steps of: (a) contacting a non-endogenous candidate compound with a GPCR Fusion Protein, the GPCR Fusion Protein comprising the endogenous, constitutively active CXCR3 and a G protein; and (b) determining whether a receptor functionality is modulated, wherein a change in receptor functionality is indicative of the candidate compound being an agonist, inverse agonist, partial agonist or antagonist of said endogenous, constitutively active CXCR3.

In some aspects the present invention is directed to methods for modulating a physiological process in primates, including but not limited to humans and non-human primates; as well as other mammals, including but not limited to, dogs, cats, rats, mice, horses, sheep, pigs, and cows. The methods comprise the steps of: (a) subjecting an endogenous CXCR3 to constitutive receptor activation to create a non-endogenous, constitutively activated CXCR3; (b) contacting the non-endogenous candidate compound with the non-endogenous, constitutively activated GPCR; (c) identifying the non-endogenous candidate compound as an agonist, an inverse agonist, a partial agonist or antagonist to the non-endogenous constitutively activated CXCR3 by measuring a difference in an intracellular signal induced by the contacted compound as compared with an intracellular signal in the absence of the contacted compound; and (d) contacting the mammal with the inverse agonist or agonist; whereby the physiological process is modulated.

In other aspects the present invention is directed to a mammal comprising a non-endogenous, constitutively activated G protein-coupled receptor (GPCR). In some embodiments, the G protein-coupled receptor has an amino acid sequence of SEQ ID NO: 6. In some embodiments, the G protein-coupled receptor is encoded by a nucleotide sequence of SEQ ID NO: 5.

DETAILED DESCRIPTION

Figure 1:
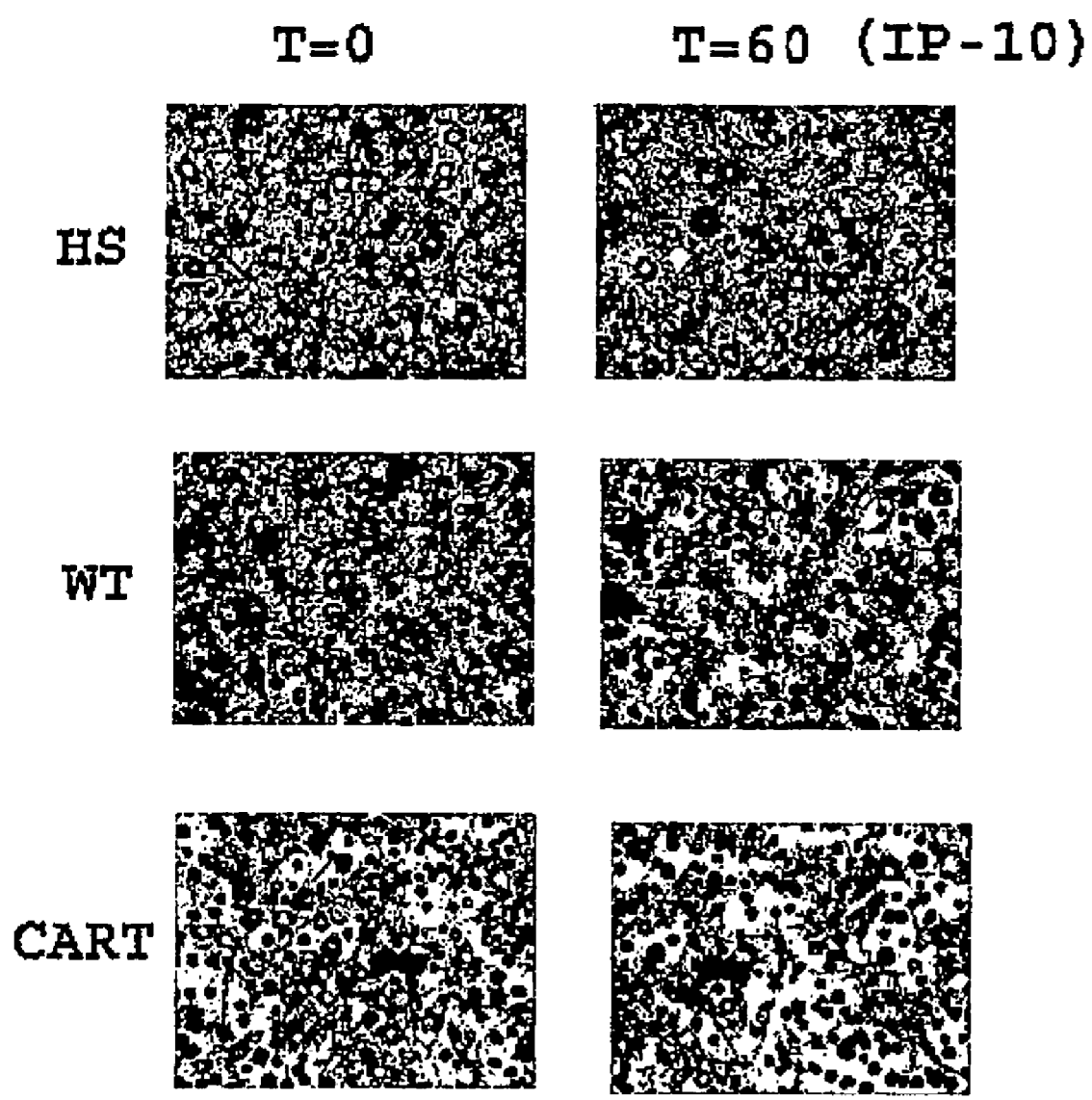
FIG. 1 shows pictures of melanophores that were either mock transfected (HS) or transfected with 20 ug of endogenous and non-endogenous CXCR3 DNA at time 0 and time 60 minutes post transfection in CFM in the absence and presence of IP-10, an agonist of CXCR3. The cells were exposed to light for approximately one hour prior to photographing. There is a similarity in morphology between the two sets of cells. In the absence of IP-10, mock-transfected cells and cells tranfected with the endogenous CXCR3 ("wild-type"), as expected, retained the normal pigment-dispersed phenotype while the cells transfected with non-endogenous CXCR3 ("CART") were substantially aggregated. Comparing the cells containing the wild-type and the cells containing CART in the presence of IP-10, the cells containing CART respond more appropriately by aggregating their pigment.

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean materials (e.g., ligands, candidate compounds) that activate the intracellular response when they bind to the receptor, or enhance GTP binding to membranes. In some embodiments, AGONISTS are those materials not previously known to activate the intracellular response when they bind to the receptor or to enhance GTP binding to membranes.

ALLOSTERIC MODULATORS shall mean materials (e.g., ligands, candidate compounds) that affect the functional activity of the receptor but which do not inhibit the endogenous ligand from binding to the receptor. Allosteric modulators include inverse agonists, partial agonists and agonists.

AMINO ACID ABBREVIATIONS used herein are set out in Table A:

TABLE A

| ALANINE | ALA | A |
|---|---|---|
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONIST shall mean materials (e.g., ligands, candidate compounds) that competitively bind to the receptor at the same site as the agonists but which do not activate the intracellular response initiated by the active form of the receptor, and can thereby inhibit the intracellular responses by agonists. ANTAGONISTS do not diminish the baseline intracellular response in the absence of an agonist. In some embodiments, ANTAGONISTS are those materials not previously known to activate the intracellular response when they bind to the receptor or to enhance GTP binding to membranes.

CANDIDATE COMPOUND shall mean a molecule (for example, and not limitation, a chemical compound) that is amenable to a screening technique. Preferably, the phrase "candidate compound" does not include compounds which were publicly known to be compounds selected from the group consisting of inverse agonist, agonist or antagonist to a receptor, as previously determined by an indirect identification process ("indirectly identified compound"); more preferably, not including an indirectly identified compound which has previously been determined to have therapeutic efficacy in at least one mammal; and, most preferably, not including an indirectly identified compound which has previously been determined to have therapeutic utility in humans.

COMPOSITION means a material comprising at least one component; a "pharmaceutical composition" is an example of a composition.

COMPOUND EFFICACY shall mean a measurement of the ability of a compound to inhibit or stimulate receptor functionality; i.e. the ability to activate/inhibit a signal transduction pathway, as opposed to receptor binding affinity. Exemplary means of detecting compound efficacy are disclosed in the Example section of this patent document.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

CONSTITUTIVELY ACTIVATED RECEPTOR shall mean a receptor subjected to constitutive receptor activation. A constitutively activated receptor can be endogenous or non-endogenous.

CONSTITUTE RECEPTOR ACTIVATION shall mean stabilization of a receptor in the active state by means other than binding of the receptor with its ligand or a chemical equivalent thereof.

CONTACT or CONTACTING shall mean bringing at least two moieties together, whether in an in vitro system or an in vivo system.

DECREASE is used to refer to a reduction in a measurable quantity and is used synonymously with the terms "reduce", "diminish", "lower", and "lessen".

DIRECTLY IDENTIFYING or DIRECTLY IDENTIFIED, in relationship to the phrase "candidate compound", shall mean the screening of a candidate compound against a constitutively activated receptor, preferably a constitutively activated orphan receptor, and most preferably against a constitutively activated G protein-coupled cell surface orphan receptor, and assessing the compound efficacy of such compound. This phrase is, under no circumstances, to be interpreted or understood to be encompassed by or to encompass the phrase "indirectly identifying" or "indirectly identified."

ENDOGENOUS shall mean a material that a mammal naturally produces. ENDOGENOUS in reference to, for example and not limitation, the term "receptor," shall mean that which is naturally produced by a mammal (for example, and not limitation, a human) or a virus. By contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

EXPRESSION VECTOR shall refer to the molecules that comprise a nucleic acid sequence which encode one or more desired polypeptides and which include initiation and termination signals operably linked to regulatory elements including a promoter and polyadenylation signal capable of directing expression.

G PROTEIN COUPLED RECEPTOR FUSION PROTEIN and GPCR FUSION PROTEIN, in the context of the invention disclosed herein, each mean a non-endogenous protein comprising an endogenous, constitutively activate GPCR or a non-endogenous, constitutively activated GPCR fused to at least one G protein, most preferably the alpha ($\alpha$) subunit of such G protein (this being the subunit that binds GTP), with the G protein preferably being of the same type as the G protein that naturally couples with endogenous orphan GPCR For example, and not limitation, in an endogenous state, if the G protein "$G_s\alpha$" is the predominate G protein that couples with the GPCR, a GPCR Fusion Protein based upon the specific GPCR would be a non-endogenous protein comprising the GPCR fused to $G_s\alpha$; in some circumstances, as will be set forth below, a non-predominant G protein can be fused to the GPCR. The G protein can be fused directly to the C-terminus of the constitutively active GPCR or there may be spacers between the two.

HOST CELL shall mean a cell capable of having a Plasmid and/or Vector incorporated therein. In the case of a prokaryotic Host Cell, a Plasmid is typically replicated as a autonomous molecule as the Host Cell replicates (generally, the Plasmid is thereafter isolated for introduction into a eukaryotic Host Cell); in the case of a eukaryotic Host Cell, a Plasmid is integrated into the cellular DNA of the Host Cell such that when the eukaryotic Host Cell replicates, the Plasmid replicates. In some embodiments the Host Cell is eukaryotic, more preferably, mammalian, and most preferably selected from the group consisting of 293, 293T and COS-7 cells.

INDIRECTLY IDENTIFYING or INDIRECTLY IDENTIFIED means the traditional approach to the drug discovery process involving identification of an endogenous ligand specific for an endogenous receptor, screening of candidate compounds against the receptor for determination of those which interfere and/or compete with the ligand-receptor interaction, and assessing the efficacy of the compound for affecting at least one second messenger pathway associated with the activated receptor.

INHIBIT or INHIBITING, in relationship to the term "response" shall mean that a response is decreased or prevented in the presence of a compound as opposed to in the absence of the compound.

INVERSE AGONISTS shall mean materials (e.g., ligand, candidate compound) which bind to either the endogenous form of the receptor or to the constitutively activated form of the receptor, and which inhibit the baseline intracellular response initiated by the active form of the receptor below the normal base level of activity which is observed in the absence of agonists, or decrease GTP binding to membranes. Preferably, the baseline intracellular response is inhibited in the presence of the inverse agonist by at least 30%, at least 50%, at least 60%, at least 70%, at least 75%, at least 80%, at least 85%, at least 90%, at least 92%, at least 94%, at least 95%, at least 96%, at least 97%, at least 98%, and most preferably at least 99% as compared with the baseline response in the absence of the inverse agonist.

INTRACELLULAR SIGNAL shall mean a detectable signal transduced by a receptor. Examples of intracellular signals are well-known to the art-skilled. Intracellular signals may be endogenous, e.g. an endogenous intracellular signal including without limitation second messengers; or non-endogenous, e.g. a non-endogenous intracellular signal including without limitation a engineered signal, i.e., β-galactosidase, GUS, luciferase. Assays for detecting intracellular signals are known to those skilled in the art and include GTP-γS assays, cAMP assays; CREB assays; β-galactosidase assays; luciferase assays; DAG assays; AP1 assays; $IP_3$ assays; and adenylyl cyclase assays. In some embodiments the term INTRACELLULAR SIGNAL is used synonymously with "reporter signal".

ISOLATED shall mean that the material is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such a polynucleotide could be part of a vector and/or such a polynucleotide or polypeptide could be part of a composition, and still be isolated in that the vector or composition is not part of its natural environment.

KNOWN RECEPTOR shall mean an endogenous receptor for which the endogenous ligand specific for that receptor has been identified.

LIGAND shall mean a molecule specific for a naturally occurring receptor.

As used herein, the terms MODULATE or MODIFY are meant to refer to an increase or decrease in the amount, quality, or effect of a particular activity, function or molecule.

MUTANT or MUTATION in reference to an endogenous receptor's nucleic acid and/or amino acid sequence shall mean a specified change or changes to such endogenous sequences such that a mutated form of an endogenous non-onstitutively activated receptor evidences constitutive activation of the receptor. In terms of equivalents to specific sequences, a subsequent mutated form of a human receptor is considered to be equivalent to a first mutation of the human receptor if (a) the level of constitutive activation of the subsequent mutated form of a human receptor is substantially the same as that evidenced by the first mutation of the receptor; and (b) the percent sequence (amino acid and/or nucleic acid) homology between the subsequent mutated form of the receptor and the first mutation of the receptor is at least 80%, at least 85%, at least 90%, at least 92%, at least 94%, at least 95%, at least 96%, at least 97%, at least 98%, and most preferably at least 99%. In some embodiments, owing to the fact that some preferred cassettes disclosed herein for achieving constitutive activation include a single amino acid and/or codon change between the endogenous and the non-endogenous forms of the GPCR, it is preferred that the percent sequence homology should be at least 98%.

NON-ORPHAN RECEPTOR shall mean an endogenous naturally occurring molecule specific for an identified ligand wherein the binding of a ligand to a receptor activates an intracellular signaling pathway.

ORPHAN RECEPTOR shall mean an endogenous receptor for which the ligand specific for that receptor has not been identified or is not known.

PARTIAL AGONISTS shall mean materials (e.g., ligands, candidate compounds) that activate the intracellular response when they bind to the receptor to a lesser degree/extent than do agonists, or enhance GTP binding to membranes to a lesser degree/extent than do agonists. Preferably, the intracellular response is a lesser degree/extent than of an agonist by at least 95%, at least 80%, at least 70%, at least 60%, at least 65%, at least 50%, at least 45%, at least 40%, at least 38%, at least 35%, at least 34%, at least 33%, at least 32%, at least 31%, and most preferably at least 30% as compared with the baseline response of an agonist.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

PLASMID shall mean the combination of a Vector and cDNA. Generally, a Plasmid is introduced into a Host Cell for the purposes of replication and/or expression of the cDNA as a protein.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins. RECEPTOR FUNCTIONALITY can readily be measured by the art skilled by measuring, without limitation, intracellular signals, ion influx or efflux, gene transcription, and effect of catalytic reaction.

SECOND MESSENGER shall mean an intracellular response produced as a result of receptor activation. A second messenger can include, for example, inositol triphosphate ($IP_3$), diacycglycerol (DAG), cyclic AMP (cAMP), and cyclic GMP (cGMP). Second messenger response can be measured for a determination of receptor activation. In addition, second messenger response can be measured for the direct identification of candidate compounds, including for example, inverse agonists, partial agonists, agonists, and antagonists.

SIGNAL TO NOISE RATIO shall mean the signal generated in response to activation, amplification, or stimulation wherein the signal is above the background noise or the basal level in response to non-activation, non-amplification, or non-stimulation. In some preferred embodiments, the signal is at least 10%, preferably at least 20%, more preferably at least 30%, more preferably at least 40%, more preferably at least 50%, more preferably at least 60%, more preferably at least 70%, more preferably at least 80%, more preferably at least 90%, and most preferably at least 100% above background noise or basal level.

SPACER shall mean a translated number of amino acids that are located after the last codon or last amino acid of a gene, for example a GPCR of interest, but before the start codon or beginning regions of the G protein of interest, wherein the translated number amino acids are placed in-frame with the beginnings regions of the G protein of interest. The number of translated amino acids can be tailored according to the needs of the skilled artisan and is generally from about one amino acid, preferably two amino acids, more preferably three amino acids, more preferably four amino acids, more preferably five amino acids, more preferably six amino acids, more preferably seven amino acids, more preferably eight amino acids, more preferably nine amino acids, more preferably ten amino acids, more preferably eleven amino acids, and even more preferably twelve amino acids.

STIMULATE or STIMULATING, in relationship to the term "response" shall mean that a response is increased in the presence of a compound as opposed to in the absence of the compound.

SUBJECTING AN ENDOGENOUS GPCR TO CONSTITUTIVE RECEPTOR ACTIVATION shall refer to the steps through which a GPCR is constitutively activated.

SUBJECT shall mean primates, including but not limited to humans and non-human primates; as other mammals, including but not limited to, dogs, cats, rats, mice, horses, sheep, pigs, and cows.

SUBSTANTIALLY SIMILAR shall refer to a result that is within 40% of a control result, preferably within 35%, more preferably within 30%, more preferably within 25%, more preferably within 20%, more preferably within 15%, more preferably within 10%, more preferably within 5%, more preferably within 2%, and most preferably within 1% of a control result. For example, in the context of receptor functionality, a test receptor may exhibit SUBSTANTIALLY SIMILAR results to a control receptor if the transduced signal, measured using a method taught herein or similar method known to the art-skilled, if within 40% of the signal produced by a control signal.

VECTOR in reference to cDNA shall mean a circular DNA capable of incorporating at least one cDNA and capable of incorporation into a Host Cell.

The order of the following sections is set forth for presentational efficiency and is not intended, nor should be construed, as a limitation on the disclosure or the claims to follow.

Introduction

A. Background of CXCR3 Receptor

Chemokines constitute a family of small cytokines that are produced in inflammation and regulate leukocyte recruitment (Baggiolini, M. et al., "Interleulin-8 and related chemotactic cytokines—CXC and CC chemokines," Adv. Immunol. 55: 97-179 (1994); Springer, T. A., "Traffic signals on endothelium for lymphocyte recirculation and leukocyte emigration," Annu. Rev. Physiol. 57: 827-872 (1995); and Schall, T. J. and K. B. Bacon, "Chemokines, leukocyte trafficking, and inflammation," Curr. Opin. Inmunol. 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin upregulation, formation of bioactive lipids (e.g., leukotrienes) and respiratory burst, associated with leukocyte activation. Thus, the chemokines are early triggers of the inflanmmatory response, causing inflammatory mediator release, chemotaxis and extravasation to sites of infection or inflammation.

Chemokines act through receptors which belong to a superfamily of seven transmembrane spanning G-protein coupled receptors (Murphy, P. M., "The molecular biology of leukocyte chemoattractant receptors," Annu. Rev. Immunol., 12: 593-633 (1994); Gerard, C. and N. P. Gerard, "The proinflammatory seven transmembrane segment receptors of the leukocyte," Curr. Opin. Immunol., 6: 140-145 (1994)).

Two of these receptors, the interleukin-8 (IL-8) receptors, IL-8R1 (interleukin-8 receptor type 1; Holmes, W. E. et al., "Structure and functional expression of a human interleukin-8 receptor," Science, 253: 1278-1280 (1991)) and IL-8R2 (interleukin-8 receptor type 1; Murphy, P. M. and H. L. Tiffany, "Cloning of complementary DNA encoding a fnctional human interleukin-8 receptor," Science, 253: 1280-1283 (1991)), are largely restricted to neutrophils and recognize the NH2-terminal Glu-Leu-Arg (ELR) motif, an essential binding epitope in those CXC chemokines that induce neutrophil chemotaxis (Clark-Lewis, I. et al., "Structure-activity relationships of interleukin-8 determined using chemically synthesized analogs. Critical role of NH2-terminal residues and evidence for uncoupling of neutrophil chemotaxis, exocytosis, and receptor binding activities," J. Biol. Chem., 266: 23128-23134 (1991); Hebert, C. A. et al., "Scanning mutagenesis of interleukin-8 identifies a cluster of residues required for receptor binding," J. Biol. Chem., 266: 18989-18994 (1991); and Clark-Lewis, I. et al., "Platelet factor 4 binds to interleukin 8 receptors and activates neutrophils when its N terminus is modified with Glu-Leu-Arg," Proc. Natl. Acad. Sci. USA, 90: 3574-3577 (1993)). Five distinct CC chemokine receptors have been described, and are designated CC-CKR1, -2, -3, -4 and -5 (CC-CKR, CC chemokine receptor, Neote, K. et al., "Molecular cloning, functional expression, and signaling characteristics of a CC chemokine receptor," Cell, 72: 415-425 (1993); Gao, J. -L. et al., "Structure and functional expression of the human macrophage inflammatory protein 1.alpha./RANTES receptor," J. Exp. Med., 177: 1421-1427 (1993); Charo, I. F. et al., "Molecular cloning and functional expression of two monocyte chemoattractant protein 1 receptors reveals alternative splicing of the carboxyl-terminal tails," Proc. Natl. Acad. Sci. USA, 91: 2752-2756 (1994); Myers, S. J., et al., J. Biol. Chem., 270: 5786-5792 (1995); Combadiere, C. et al., Cloning and functional expression of a human eosinophil CC chemokine receptor," J. Biol. Chem., 270 (27): 16491-16494 (1995); and Correction, J. Biol. Chem., 270: 30235 (1995); Ponath, P. D. et al., "Molecular cloning and characterization of a human eotaxin receptor expressed selectively on eosinophils," J. Exp. Med., 183: 2437-2448 (1996); and Daugherty, B. L. et al., "Cloning, expression, and characterization of the human eosinophil eotaxin receptor," J. Exp. Med., 183: 2349-2354 (1996); Power, C. A. et al., 1995, "Molecular cloning and functional expression of a novel CC chemokine receptor cDNA from a human basophilic cell line," J. Biol. Chem., 270: 19495-19500 (1995); Hoogewerf, A. J. et al., "Molecular cloning of murine CC CKR4 and high affinity binding of chemokines to murine and human CC CKR-4," Biochem. Biophys. Res. Commun., 218: 337-343 (1996); Samson, M. et al., "Molecular cloning and functional expression of a new human CC-chemokine receptor gene," Biochemistry, 35: 3362-3367 (1996)). The CC chemokine receptors occur on several types of leukocytes, including monocytes, granulocytes and lymphocytes, and recognize CC chemokines, but not CXC chemokines.

Constitutively activated non-endogenous version of CXCR3 can be obtained, without limitation, by site-directed mutational methods. Constitutively activated receptors useful for direct identification of candidate compounds are most preferably achieved by mutating the receptor at a specific location, by way of example and not limitation, within transmembrane three (TM3) region. Such mutation can produce a non-endogenous receptor that is constitutively activated, as evidenced by an increase in the functional activity of the receptor, for example, an increase in the level of second messenger activity.

As will be set forth and disclosed in greater detail below, utilization of a mutational approach to modify the endogenous sequence of CXCR3 leads to constitutively activated versions of this receptor. This non-endogenous, constitutively activated version of CXCR3 can be utilized, inter alia, for the screening of candidate compounds to directly identify compounds which modulate processes and activities including, but not limited to, leukocyte trafficking, immune surveillance, innate and adaptive immune responses and vaious forms of pathological inflammation. Such physiological processes can further be modulated through, inter alia, subjecting an endogenous CXCR3 to constitutive receptor activation to create a non-endogenous, constitutively activated CXCR3; and contacting the non-endogenous, constitutively activated CXCR3 with a non-endogenous agonist, inverse agonist, partial agonist or antagonist of the receptor, or, in other embodiments, by subjecting an endogenous CXCR3 to constitutive receptor activation to create a non-endogenous, constitutively activated CXCR3, whereby the physiological process is modulated.

B. Receptor Screening

Screening candidate compounds against a non-endogenous, constitutively activated version of the GPCR disclosed herein allows for the direct identification of candidate compounds which act at the cell surface of the receptor, without requiring use of the receptor's endogenous ligand. This patent document discloses a mutational approach for creating non-endogenous, constitutively activated version of CXCR3. With the disclosed techniques, one skilled in the art is credited with the ability to create such constitutively activated versions of CXCR3 for the uses disclosed herein, as well as other uses.

C. Disease/Disorder Identification and/or Selection

As will be set forth in greater detail below, most preferably inverse agonists, partial agonists and agonists in the form of small molecule chemical compounds to the non-endogenous, constitutively activated GPCR can be identified by the methodologies of this invention. Such compounds are ideal candidates as lead modulators in drug discovery programs for treating diseases or disorders associated with a particular receptor. The ability to directly identify such compounds to the GPCR, in the absence of use of the receptor's endogenous ligand, allows for the development of pharmaceutical compositions.

Preferably, in situations where it is unclear what disease or disorder may be associated with a receptor; the DNA sequence of the GPCR is used to make a probe for (a) dot-blot analysis against tissue-mRNA, and/or (b) RT-PCR identification of the expression of the receptor in tissue samples. The presence of a receptor in a tissue source, or a diseased tissue, or the presence of the receptor at elevated concentrations in diseased tissue compared to a normal tissue, can be preferably utilized to identify a correlation with a treatment regimen, including but not limited to, a disease associated with that disease. Receptors can equally well be localized to regions of organs by this technique. Based on the known functions of the specific tissues to which the receptor is localized, the putative functional role of the receptor can be deduced.

D. Screening of Candidate Compounds

1. Generic GPCR Screening Assay Techniques

When a G protein receptor becomes constitutively active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTγS can be used to monitor G protein coupling to membranes in the absence and presence of ligand. An example of this monitoring, among other examples well-known and available to those in the art, was reported by Traynor and Nahorsid in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit this enzyme. Adenylyl cyclase catalyzes the conversion of ATP to cAMP; thus, constitutively activated GPCRs that couple the Gs protein are associated with increased cellular levels of cAMP. On the other hand, constitutively activated GPCRs that couple Gi (or Gz, Go) protein are associated with decreased cellular levels of cAMP. See, generally, "Indirect Mechanisms of Synaptic Transmission," Chpt. 8, From Neuron To Brain ($3^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq

Gq and Go are associated with activation of the enzyme phospholipase C, which in turn hydrolyzes the phospholipid $PIP_2$, releasing two intracellular messengers: diacycloglycerol (DAG) and inistol 1,4,5-triphoisphate ($IP_3$). Increased accumulation of $IP_3$ is associated with activation of Gq- and Go-associated receptors. See, generally, "Indirect Mechanisms of Synaptic Transmission," Chpt. 8, From Neuron To Brain ($3^{rd}$ Ed.) Nichols, J. G. et al eds. Sinauer Associates, Inc. (1992). Assays that detect $IP_3$ accumulation can be utilized to determine if an candidate compound is, e.g., an inverse agonist to a Gq- or Go-associated receptor (i.e., such a compound would decrease the levels of $IP_3$). Gq-associated receptors can also be examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. Ligand-Based Confirmation Assays

The candidate compounds directly identified using the techniques (or equivalent techniques) above are then, most preferably, verified using a ligand-based verification assay, such as the one set forth in the protocol of Example 7. The importance here is that the candidate compound be directly identified; subsequent confirmation, if any, using the endogenous ligand, is merely to confirm that the directly identified candidate compound has targeted the receptor.

4. GPCR Fusion Protein

The use of a non-endogenous, constitutively activated GPCR, for use in screening of candidate compounds for the direct identification of inverse agonists, agonists and partial agonists, provides an interesting screening challenge in that, by definition, the receptor is active even in the absence of an endogenous ligand bound thereto. Thus, in order to differentiate between, e.g. the non-endogenous receptor in the presence of a candidate compound and the non-endogenous receptor in the absence of that compound, with an aim of such a differentiation to allow for an understanding as to whether such compound may be an inverse agonist, agonist, partial agonist or has no affect on such a receptor, it is preferred that an approach be utilized that can enhance such differentiation. A preferred approach is the use of a GPCR Fusion Protein.

Generally, once it is determined that a non-endogenous GPCR has been constitutively activated using the assay techniques set forth above (as well as others), it is possible to determine the predominant G protein that couples with the endogenous GPCR. Coupling of the G protein to the GPCR provides a signaling pathway that can be assessed. Because it is most preferred that screening take place by use of a mammalian expression system, such a system will be expected to have endogenous G protein therein. Thus, by definition, in such a system, the non-endogenous, constitutively activated GPCR will continuously signal. In this regard, it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the non-endogenous GPCR. The GPCR Fusion Protein is preferred for screening with a non-endogenous, constitutively activated GPCR because such an approach increases the signal that is most preferably utilized in such screening techniques. This is important in facilitating a significant "signal to noise" ratio, such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. The criteria of importance for such a GPCR Fusion Protein construct is that the endogenous GPCR sequence and the G protein sequence both be in-frame (preferably, the sequence for the endogenous GPCR is upstream of the G protein sequence) and that the "stop" codon of the GPCR must be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Use of a spacer is preferred (based upon convenience) in that some restriction sites that are not used will, effectively, upon expression, become a spacer. Most preferably, the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct) be available for insertion of an endogenous GPCR sequence therein; this provides for efficiency in the context of large-scale screening of a variety of different endogenous GPCRs having different sequences.

E. Co-transfection of a Target Gi Coupled GPCR with a Signal-Enhancer Gs Coupled GPCR (cAMP Based Assays)

A Gi coupled receptor is known to inhibit adenylyl cyclase, and, therefore, decrease the level of cAMP production, which can make assessment of cAMP levels challenging. An effective technique in measuring the decrease in production of cAMP as an indication of constitutive activation of a receptor that predominantly couples Gi upon activation can be accomplished by co-transfecting a signal enhancer, e.g., a non-endogenous, constitutively activated receptor that predominantly couples with Gs upon activation (e.g., TSHR-A623I, disclosed below), with the Gi linked GPCR. As is apparent, constitutive activation of a Gs coupled receptor can be determined based upon an increase in production of cAMP. Constitutive activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with the endogenous Gi coupled receptor (the "target receptor") provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with a constitutively activated version of the target receptor, cAMP would be expected to further decrease (relative to base line) due to the increased functional activity of the Gi target (i.e., which decreases cAMP).

Screening of candidate compounds using a cAMP based assay can then be accomplished, with two provisos: first, relative to the Gi coupled target receptor, "opposite" effects will result, i.e., an inverse agonist of the Gi coupled target receptor will increase the measured cAMP signal, while an agonist of the Gi coupled target receptor will decrease this signal; second, as would be apparent, candidate compounds that are directly identified using this approach should be assessed independently to ensure that these do not target the signal enhancing receptor (this can be done prior to or after screening against the co-transfected receptors).

F. Medicinal Chemistry

Generally, but not always, direct identification of candidate compounds is preferably conducted in conjunction with compounds generated via combinatorial chemistry techniques, whereby thousands of compounds are randomly prepared for such analysis. Generally, the results of such screening will be compounds having unique core structures; thereafter, these compounds are preferably subjected to additional chemical modification around a preferred core structure(s) to further enhance the medicinal properties thereof. Such techniques are known to those in the art and will not be addressed in detail in this patent document.

G. Pharmaceutical Compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, $16^{th}$ Edition, 1980, Mack Publishing Co., (Oslo et al., eds.).

H. Other Utility

Although a preferred use of the non-endogenous version of the known CXCR3 disclosed herein may be for the direct identification of candidate compounds as inverse agonists, agonists partial agonists or antagonist (preferably for use as pharmaceutical agents), this version of known CXCR3 can also be utilized in research settings. For example, in vitro and in vivo systems incorporating GPCRs can be utilized to further elucidate and better understand the roles these receptors play in the human condition, both normal and diseased, as well as understanding the role of constitutive activation as it applies to understanding the signaling cascade. Other uses of the disclosed receptors will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below.

Example 1

Preparation of Endogenous GPCR: CXCR3

The cDNA for human CXCR3 was generated and cloned into pCMV expression vector as follows: PCR was performed using a clone (provided by Brian O'Dowd) as template and pfu polymerase (Stratagene) with the buffer system provided by the manufacturer supplemented with 10% DMSO, 0.25 µM of each primer, and 0.5 mM of each of the 4 nucleotides. The cycle condition was 25 cycles of: 94° C. for 1 min; 56° C. for 1 min; and 72° C. for 2.5 min. The 5' PCR primer contained an EcoRI site with the sequence:

```
                                          (SEQ.ID.NO.:3)
5'-ACGAATTCAGCCATGGTCCTTGAGGTGAGTGACCACCAAGTGCTAAA
T-3'
``` and the 3' primer contained a BamHI site with the sequence

```
                                          (SEQ.ID.NO.:4)
5'-GAGGATCCTGGAATGCGGGGAAGTCAG-3'.
```

The 1.2 kb PCR fragment was digested with EcoRI and cloned into EcoRI-SmaI site of pCMV expression vector. Nucleic acid (SEQ. ID. NO.: 1) and amino acid (SEQ. ID. NO.: 2) sequences for human CXCR3 were thereafter determined and verified.

Example 2

Preparation of Non-Endogenous Versions of GPCR: CXCR3

Those skilled in the art are credited with the ability to select techniques for mutation of a nucleic acid sequence. Preparation of the non-endogenous, constitutively activated human CXCR3 receptor was accomplished by creating a N134S mutation (see, SEQ. ID. NO.:5 for nucleic acid sequence, and SEQ. ID. NO.:6 for amino acid sequence). Mutagenesis was performed using Transformer Site-Directed™ Mutagenesis Kit (Clontech) according to manufacturer's instructions. The two mutagenesis primers utilized had the following sequences:

```
                                          (SEQ.ID.NO.:7)
5'-CCCTCTTCAACATCAgCTTCTACGCAGGAGC-3'

(SEQ.ID.NO.:8)
5'-GCTCCTGCGTAGAAGcTGATGTTGAAGAGGG-3'.
```

The resulting 1.2 kb PCR fragment was digested with EcoRI and cloned into blunt-EcoRI site of pCMV expression vector. Nucleic acid (SEQ. ID. NO.:5) and amino acid (SEQ. ID. NO.:6) sequences for CXCR3 were thereafter determined and verified.

Both the endogenous and non-endogenous versions of CXCR3 were double tagged with 5'-HA and 3'-V5.

Assessment of constitutive activity of the non-endogenous versions of human CXCR3 was then accomplished. See, Example 4 below:

Example 3

Receptor Expression

A variety of cells are available to the art for the expression of proteins, however for purposes of this patent document, *Xenopus oocyte* and mammalian cells are preferred.

1. Transient Transfection

Functional expression of endogneous and non-endogenous versions of CXCR3 were evaluated in transiently transfected melanophores using standard protocols. The current cell type used for studies are denoted as clone 10 (c10). These cells were a derived population from the human $\beta_2$-adrenergic expressing melanophore cell line. These cells were specifically chosen due to their more plate-like appearance and because they have a greater dynamic-range in terms of pigment movement than even the parent plate-like cells. Ultimately assay development and optimization is cell type dependent and must be evaluated for each GPCR target as well as cell line used. Briefly, cells were harvested from flasks (T-185 $cm^2$ flask) using Trypsin (0.7x), and transfected by electroporation. Cells were preplated in flasks approximately 3-4 hours to rid of non-viable cells and debris. Upon completion, flasks were subsequently trypsinized and plated onto 96 well poly-D-lysine coated plates for assay. All assays were run 48 hours post transfection and assessed for constitutive Gs/Gq or Gi coupling. As a control, mock transfected cells were electroporated with various concentrations of salmon sperm (SS) DNA alone or herring sperm (HS). This melanophore mock transfected data depicts the dynamic range of both dispersion and aggregation in the absence of expressed CXCR3 receptor in melanophores. FIG. 1 shows pictures of melanophores that were either mock transfected (HS) or transfected with 20 ug of endogenous and non-endogenous CXCR3 DNA at time 0 and time 60 hours post trasfection in CFM. The cells were exposed to light for approximately one hour prior to photographing. There is a similarity in morphology between the two sets of cells. In the absence of IP-10, mock-transfected cells and cells tranfected with the non-endogenous,CXCR3 ("wild-type"), as expected, retained the normal pigment-dispersed phenotype while the cells transfected with non-endogenous CXCR3 ("CART") were substantially aggregated. Comparing the cells containing the wild-type and the cells containing CART in the presence of IP-10, the cells containing CART respond more appropriately by aggregating their pigment.

2. Stable Cell Lines

Approximately 12×10⁶ 293 cells are plated on a 15 cm tissue culture plate. Grown in DME High Glucose Medium containing ten percent fetal bovine serum and one percent sodium pyruvate, L-glutarine, and anti-biotics. Twenty-four hours following plating of 293 cells (or to ~80% confluency), the cells are transfected using 12 µg of DNA. The 12 µg of DNA is combined with 60 µl of lipofectamine and 2 mL of DME High Glucose Medium without serum. The medium is aspirated from the plates and the cells are washed once with medium without serum. The DNA, lipofectamine, and medium mixture are added to the plate along with 10 mL of medium without serum. Following incubation at 37 degrees Celsius for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/mL. The transfected cells will undergo selection for positively transfected cells containing the G418 resistant gene. The medium is replaced every four to five days as selection occurs. During selection, cells are grown to create stable pools, or split for stable clonal selection.

Example 4

Assays for Determination of Constitutive Activity of Non-Endogenous CXCR3

A variety of approaches are available for assessment of constitutive activity of the non-endogenous version of human CXCR3. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Constitutively activated receptors continue to exchange GDP for GTP. The non-hydrolyzable GTP analog, [$^{35}$S]GTPγS, can be utilized to demonstrate enhanced binding of [$^{35}$S]GTPγS to membranes expressing constitutively activated receptors. The advantage of using [$^{35}$S]GTPγS binding to measure constitutive activation is that: (a) it is generically applicable to all G protein-coupled receptors; (b) it is proximal at the membrane surface maling it less likely to pick-up molecules which affect the intracellular cascade.

This assay utilizes the ability of G protein coupled receptors to stimulate [$^{35}$S]GTPγS binding to membranes expressing the relevant receptors. The assay can, therefore, be used in the direct identification method to screen candidate compounds to known, orphan and constitutively activated G protein-coupled receptors. The assay is generic and has application to drug discovery at all G protein-coupled receptors.

The [$^{35}$S]GTPγS is incubated in 20 mM HEPES and between 1 and about 20 mM MgCl$_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred ) and 12.5 to 75 µg membrane protein (e.g, 293 cells expressing the Gs Fusion Protein; this amount can be adjusted for optimization) and 10 µM GDP (this amount can be changed for optimization) for 1 hour. Wheatgerm agglutinin beads (25 µl; Amersham) are then added and the mixture incubated for another 30 minutes at room temperature. The tubes are then centrifuged at 1500×g for 5 minutes at room temperature and then counted in a scintillation counter.

2. Cell-Based cAMP Detection Assay

In the following assay, a 96-well Adenylyl Cyclase Activation Flashplate is used (NEN: #SMP004A). First, 50 ul of the standards for the assay is added to the plate, in duplicate, ranging from concentrations of 50 pmol to zero pmol cAMP per well. The standard cAMP (NEN: #SMP004A) is reconstituted in water, and serial dilutions are made using 1×PBS (Irvine Scientific: #9240). Next, 50 ul of the stimulation buffer (NEN: #SMP004A) is added to all wells. Various final concentrations are used ranging from 1 uM up to 1 mM. Adenosine 5'-triphosphate, ATP, (Research Biochemicals International: #A-141) and Adenosine 5'-diphosphate, ADP, (Sigma: #A2754) are used in the assay. Next, the 293 cells transfected with 12 ug (per 150 mm tissue culture plate) of the respective cDNA (CMV or CXCR3) are harvested 24 hours post-transfection. The media is aspirated and the cells are washed once with 1×PBS. Then 5 ml of 1×PBS is added to the cells along with 3 ml of cell dissociation buffer (Sigma: #C-1544). The detached cells are transferred to a centrifuge tube and centrifuged at room temperature for five minutes. The supernatant is then removed and the cell pellet resuspended in an appropriate amount of 1×PBS to obtain a final volume of 2×10⁶ cells per milliliter.

The plate is incubated on a shaker for 15 minutes at room temperature. The detection buffer containing the tracer cAMP is prepared. In 11 ml of detection buffer (NEN: #SMP004A), 50 ul (equal to 1 uCi) of [$^{125}$I]cAMP (NEN: #SMP004A) is added. Following incubation, 50 ul of this detection buffer containing tracer cAMP is added to each well. The plate is then placed on a shaker and incubated at room temperature for two hours. Finally, the solution from the wells of the plate is aspirated and the flashplate counted using the Wallac MicroBeta plate reader.

3. Alpha Screen

The media from Example 3(2) above is aspirated and rinsed 1× with PBS (5-10 ml/flask). 10-20 mls of PBS is then added to each flask and let sit for 2-5 minutes. The cells are pipetted off into conocal tubes for spinning for 5 minutes at 1500 rpm. PBS is aspirated and re-suspended with Stimulation Buffer (1×HBSS, 0.5 mM IBMX, 5 mM Hepes and 0.11% BSA). 2% DMSO is used to dilute the Hepes Buffer and 10 µl/well of cells at 15,000 cells/well is then added to the wells and incubated for 30 minutes. 5 µl/well of cAMP Acceptor Beads (Perlin Elmer Product No. 6760600R) are added to the wells for a final concentration of 15 µg/ml. The wells are covered and left to incubate for two hours at room temperature. 5 µl of Assay Reaction Mixture are added. The Assay Reaction Mixture is prepared by mixing the Donor Bead (Perkin Elmer Product No. 6760600R) with a final concentration of 20 µg/ml, Biotinylated cAMP Mix (Perkin Elmer Product No. 6760600R) with a final concentration of 10 nM, and Lysis Buffer (5 nM Hepes and 0.18% Igapel). The wells are then covered and incubated for two hours at room temperature. Following incubation, the wells are read on Alpha Quest and measured for light units. The light unit is then converted to pmol cAMP/well by taling the cAMP concentration and determining the pmol/well of cAMP and using the linear regretion function found on GraphPad Prism version 3.00 for Windows, GraphPad Software, San Diego Calif. USA, the light units are converted to pmol cAMP/well.

4. Cell-Based cAMP for Gi Coupled Target GPCRs

TSHR is a Gs coupled GPCR that causes the accumulation of cAMP upon activation. TSHR is constitutively activated by mutating amino acid residue 623 (i.e., changing an alanine residue to an isoleucine residue). A $G_i$ coupled receptor is expected to inhibit adenylyl cyclase, and, therefore, decrease the level of cAMP production, which can make assessment of cAMP levels challenging. An effective technique for measuring the decrease in production of cAMP as an indication of constitutive activation of a $G_i$ coupled receptor can be accomplished by co-transfecting, most preferably, non-endogenous, constitutively activated TSHR (TSHR-A623I) (or an endogenous, constitutively active $G_s$ coupled receptor) as a "signal enhancer" with a $G_i$ linked target GPCR to establish a baseline level of cAMP. Upon creating a non-endogenous version of the $G_i$ coupled receptor, this non-endogenous version of the target GPCR is then co-transfected with the signal enhancer, and it is this material that can be used for screening. We will utilize such approach to effectively generate a signal when a cAMP assay is used; this approach is preferably used in the direct identification of candidate compounds against $G_i$ coupled receptors. It is noted that for a $G_i$ coupled GPCR, when this approach is used, an inverse agonist of the target GPCR will increase the cAMP signal and an agonist will decrease the cAMP signal.

On day one, $2 \times 10^4$ 293 cells is plated out. On day two, two reaction tubes are prepared (the proportions to follow for each tube are per plate): tube A is prepared by mixing 2 µg DNA of each receptor transfected into the mammalian cells, for a total of 4 µg DNA (e.g., pCMV vector; pCMV vector with mutated THSR (TSHR-A623I); TSHR-A623I and GPCR, etc.) in 1.2 ml serum free DMEM (Ivine Scientific, Irvine, Calif.); tube B is prepared by mixing 120 µl lipofectamine (Gibco BRL) in 1.2 ml serum free DMEM. Tubes A and B are admixed by inversions (several times), followed by incubation at room temperature for 30-45 min. The admixture is referred to as the "transfection mixture". Plated 293 cells are washed with 1xPBS, followed by addition of 10 ml serum free DMEM. 2.4 ml of the transfection mixture is then added to the cells, followed by incubation for 4 hrs at 37° C./5% $CO_2$. The transfection mixture is removed by aspiration, followed by the addition of 25 ml of DMEM/10% Fetal Bovine Serum. Cells are incubated at 37° C./5% $CO_2$. After 24 hr incubation, cells are then harvested and utilized for analysis.

A Flash Plate™ Adenylyl Cyclase kit (New England Nuclear; Cat. No. SMP004A) is designed for cell-based assays, however, the kit can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 min. The cell pellet is carefully re-suspended into an appropriate volume of PBS (about 3 ml/plate). The cells are counted using a hemocytometer and additional PBS is added to give the appropriate number of cells (with a final volume of about 50 µl/well).

cAMP standards and Detection Buffer (comprising 1 µCi of tracer [$^{125}$I cAMP (50 µl] to 11 ml Detection Buffer) are prepared and maintained in accordance with the manufacturer's instructions. Assay Buffer should be prepared fresh for screening and contained 50 µl of Stimulation Buffer, 3 µl of test compound (12 µM final assay concentration) and 50 µl cells, Assay Buffer can be stored on ice until utilized. The assay can be initiated by addition of 50 µl of cAMP standards to appropriate wells followed by addition of 50 µl of PBSA to wells H-11 and H12. Fifty µl of Stimulation Buffer is added to all wells. Selected compounds are added to appropriate wells using a pin tool capable of dispensing 3 µl of compound solution, with a final assay concentration of 12 µM test compound and 100 µl total assay volume. The cells are added to the wells and incubated for 60 min at room temperature. 100 µl of Detection Mix containing tracer cAMP is then added to the wells. Plates are incubated additional 2 hours followed by counting in a Wallac MicroBeta scintillation counter. Values of cAMP/well are then extrapolated from a standard cAMP curve which is contained within each assay plate.

5. Reporter-Based Assays a. CRE-Luc Reporter Assay (Gs-Associated Receptors)

293 and 293T cells are plated-out on 96 well plates at a density of $2 \times 10^4$ cells per well and transfected using Lipofectamine Reagent (BRL) the following day according to manufacturer instructions. A DNA/lipid mixture is prepared for each 6-well transfection as follows: 260 ng of plasmid DNA in 100 µl of DMEM is gently mixed with 2 µl of lipid in 100 µl of DMEM (the 260 ng of plasmid DNA consisted of 200 ng of a 8xCRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8XCRE-Luc reporter plasmid is prepared as follows: vector SRIF-β-gal was obtained by cloning the rat somatostatin promoter (−71/+51) at Bg1V-HindIII site in the pβgal-Basic Vector (Clontech). Eight (8) copies of cAMP response element will be obtained by PCR from an adenovirus template AdpCF126CCRE8 (see, 7 *Human Gene Therapy* 1883 (1996)) and cloned into the SRIF-β-gal vector at the Kpn-Bg1V site, resulting in the 8xCRE-β-gal reporter vector. The 8xCRE-Luc reporter plasmid is generated by replacing the beta-galactosidase gene in the 8xCRE-β-gal reporter vector with the luciferase gene obtained from the pGL3-basic vector (Promega) at the HindIII-BamHI site. Following 30 min. incubation at room temperature, the DNA/lipid mixture is diluted with 400 µl of DMEM and 100 µl of the diluted mixture is added to each well. 100 µl of DMEM with 10% FCS is added to each well after a 4 hr incubation in a cell culture incubator. The following day the transfected cells are changed with 200 µl/well of DMEM with 10% FCS. Eight (8) hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue # 219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP.

c. SRF-Luc Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with 1 µM Angiotensin, where indicated. Cells are then lysed and assayed for luciferase activity using a Luclite™ Kit (Packard, Cat. # 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. Intracellular $IP_3$ Accumulation Assay ($G_q$-Associated Receptors)

Figure 3:
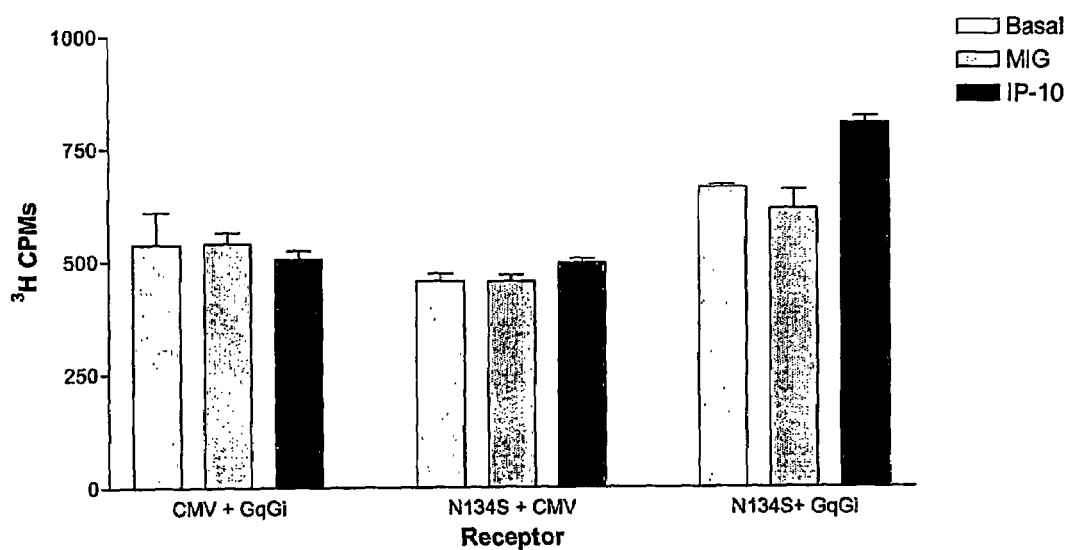
FIG. 3 is a graphic representation of CXCR3 in a second messenger assay measuring the accumulation of inositol phosphate ($IP_3$) utilizing 293 cells and comparing non-endogenous version of CXCR3 (N134S); non-endogenous version of CXCR3 (N134S) co-transfected with $G_q$(del)/$G_i$ construct; and Gq(del)/Gi construct as the control, in the presence of both γ-interferon inducible protein-10 (IP-10) and monokine inducible γ-interferon ("Mig").

On day 1, cells comprising the receptors (endogenous and/ or non-endogenous) were plated onto 24 well plates, usually $1 \times 10^5$ cells/well (although his number can be optimized. On day 2 cells were transfected by firstly mixing 0.25 µg DNA in 50 µl serum free DMEM/well and 2 µl lipofectamine in 50 µl senunfree DMEM/well. The solutions were gently mixed and incubated for 15-30 min at room temperature. Cells were washed with 0.5 ml PBS and 400 µl of serum free media was mixed with the transfection media and added to the cells. The cells were then incubated for 3-4 hrs at 37° C./5% $CO_2$ and then the transfection media was removed and replaced with 1 ml/well of regular growth media. On day 3 the cells were labeled with $^3$H-myo-inositol. Briefly, the media was removed and the cells were washed with 0.5 ml PBS. Then 0.5 ml inositol-free/serum free media (GIBCO BRL) was added/ well with 0.25 µCi of $^3$H-myo-inositol/well and the cells were incubated for 16-18 hrs o/n at 37° C./5% $CO_2$. On Day 4 the cells were washed with 0.5 ml PBS and 0.45 ml of assay medium was added containing inositol-free/serum free media 10 µM pargyline 10 mM lithium chloride or 0.4 ml of assay medium and 50 µl of 10× ketanserin ket) to final concentration of 10 µM. The cells were then incubated for 30 min at 37° C. The cells were then washed with 0.5 ml PBS and 200 µl of fresh/ice cold stop solution (1M KOH; 18 mM Na-borate; 3.8 mM EDTA) was added/well. The solution was kept on ice for 5-10 min or until cells were lysed and then neutralized by 200 µl of fresh/ice cold neutralization sol. (7.5% HCL). The lysate was then transferred into 1.5 ml eppendorf tubes and 1 ml of chloroform/methanol (1:2) was added/tube. The solution was vortexed for 15 sec and the upper phase was applied to a Biorad AG1-X8™ anion exchange resin (100-200 mesh). Firstly, the resin was washed with water at 1:1.25 W/V and 0.9 ml of upper phase is loaded onto the column. The column was washed with 10 mls of 5 mM myo-inositol and 10 ml of 5 mM Na-borate/60 mM Na-formate. The inositol tris phosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at 4° C. in water. Reference is made to FIG. 3.

In FIG. 3, CXCR3 was assayed measuring the accumulation of inositol phosphate ($IP_3$) utilizing 293 cells and comparing non-endogenous version of CXCR3 (N134S); non-endogenous version of CXCR3 (N134S) co-transfected with $G_q(del)/G_i$ construct; and Gq(del)/Gi construct, as a control, in the presence of both γ-interferon inducible protein-10 (IP-10) and monokine inducible γ-interferon ("Mig").

6. ELISA Based Method for Quantitation of HA-Tagged CXCR3

Melanophores cells were prepared according to Example 3(1) above and were transferred by trysinizastion from their culture flask to 96 well plates. The culture media was then removed from the culture flask and rinsed once with sterile PBS and aspirated. 5 ml of trysin-EDTA was then added to the flask. Once the cells have detached from the plates, the cells were then transferred to a sterile collection tube where 10 ml of media containing FBS was added to the tube. The cells were centrifuged at 3000×g for 5 minutes and the media was aspirated, followed by resuspension of the cells in a small volume of media and then counted. The volume was adjusted to a range of $5 \times 10^4$ to $5 \times 10^5$ cells/ml and the cells were then seeded in a flat-bottom 96-well test plate. Columns 1 and 2 of the test plate were not seeded. The cells were then left to attach the wells for 20 hours.

Figure 2:
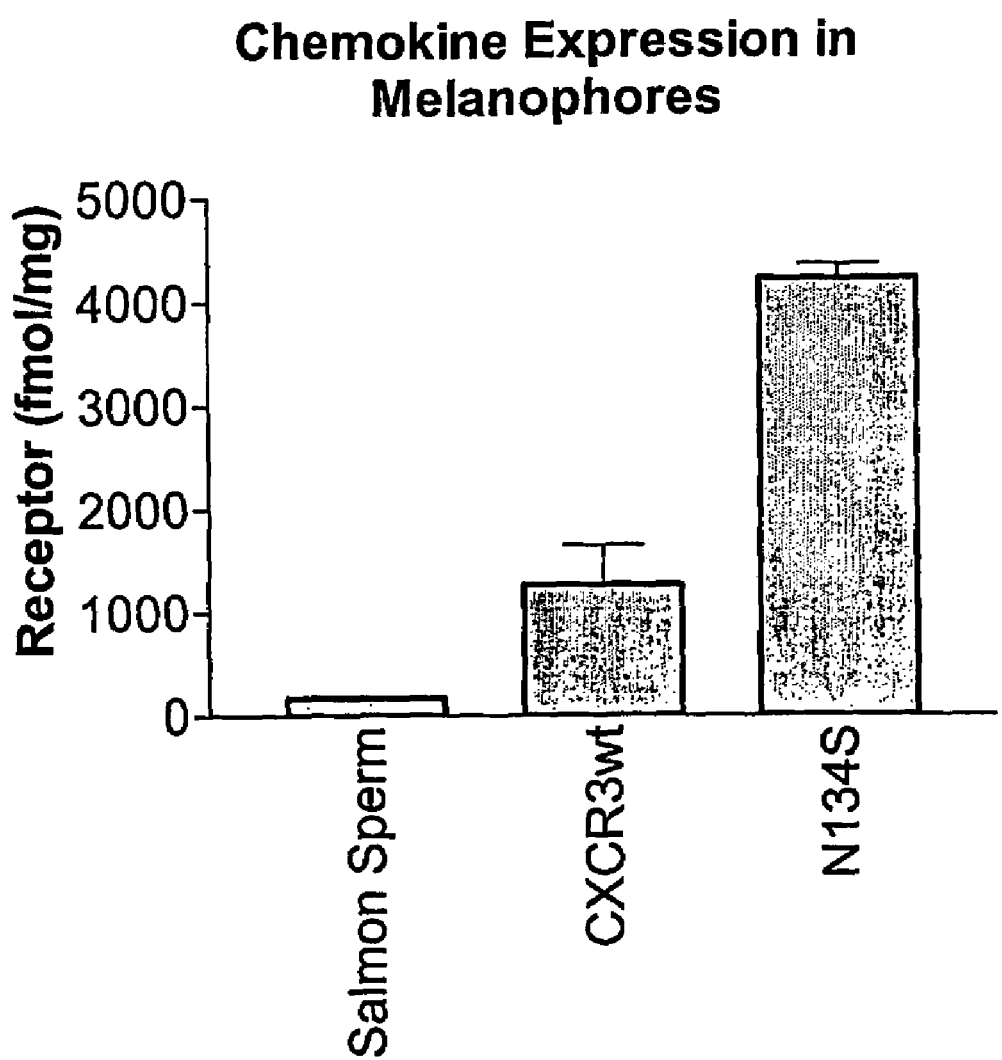
FIG. 2 is a graphic depiction of chemokine receptor expression in melanophores and comparing the endogenous version of CXCR3 ("CXCR3wt"), non-endogenous version of CXCR3 ("N134S") and a control vector ("salmon sperm") in an ELISA assay. This data evidences that the non-endogenous version of CXCR3 is constitutively activated over the endogenous version by about a 3 fold difference.

After the cells attached to the wells, the media was removed and the plate was washed one time with 200 µl per well of Wash Buffer to all wells using a multi-channel pipet. The Wash buffer was then decanted and then 100 µl per well of Fixative Solution was added only to wells containing the cells and incubated for 15 minutes at room temperature. After incubation, the liquid was removed and the plate was washed two times with 200 µl per well of Wash Buffer to all wells, followed by removal of the liquid. 100 µl per well of Primary Antibody was added to the plate using a multi-channel pippettor (Anti-HA Antibody) to all wells and allowed to incubate for 2 hours at room temperature. The liquid was then removed and washed three times with 200 µl of Wash Buffer. 100 µl of Detect Antibody (Goat Anti-Rabbit*β-galactosidase) was then added to all the wells and left to incubate for 1 hour at room temperature. The liquid was then removed and washed three times with 200 µl of Wash Buffer. 100 µl per well of Substrate (CPRG Substrate) was then added to all the wells and left to incubate for 1 to 1.5 hours at room temperature. The plate was then read and the receptor expression was quantified using Softmax method "HA.Quant.1". Reference is made to FIG. 2.

In FIG. 2, chemokine receptor was expressed in melanophores and compared with the endogenous version of CXCR3 ("CXCR3 wt"), non-endogenous version of CXCR3 ("N134S") and a control vector ("salmon sperm") in an ELISA assay. This data evidences that the non-endogenous version of CXCR3 is constitutively active over the endogenous version by about a 3 fold difference.

Example 5

Fusion Protein Preparation

1. GPCR:Gs Fusion Construct

The design of the constitutively activated GPCR-G protein fusion construct can be accomplished as follows: both the 5' and 3' ends of the rat G protein Gsα (long form; Itoh, H. et al., 83 PNAS 3776 (1986)) are engineered to include a HindIII (5'-AAGCTT-3') sequence thereon. Following confirmation of the correct sequence (including the flanking HindIII sequences), the entire sequence is shuttled into pcDNA3.1(−) (Invitrogen, cat. no. V795-20) by subdloning using the HindIII restriction site of that vector. The correct orientation for the $G_s\alpha$ sequence is determined after subcloning into pcDNA3.1(−). The modified pcDNA3.1(−) containing the rat $G_s\alpha$ gene at HinIII sequence is then verified; this vector is now available as a "universal" $G_s\alpha$ protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

PCR is then utilized to secure the respective receptor sequences for fusion within the Gsα universal vector disclosed above, using the following protocol for each: 100 ng cDNA is added to separate tubes containing 2 µl of each primer (sense and anti-sense), 3 µL of 10 mM dNTPs, 10 µL of 10 XTaqPlus™ Precision buffer, 1 µL of TaqPlus™ Precision polymerase (Stratagene: #600211), and 80 µL of water. Reaction temperatures and cycle times are as follows with cycle steps 2 through 4 were repeated 35 times: 94° C. for 1 min; 94° C. for 30 seconds; 62° C. for 20 sec; 72° C. 1 min 40 sec; and 72° C. 5 min. PCR product is then ran on a 1% agarose gel and purified. The purified product is then digested with XbaI and EcoRV and the desired inserts purified and ligated into the Gs universal vector at the respective restriction site. The positive clones are isolated following transformation and determined by restriction enzyme digest; expression using 293 cells is accomplished following the protocol set forth infra. Each positive clone for GPCR-Gs Fusion Protein is then sequenced to verify correctness.

2. Gq(6 Amino Acid Deletion)/Gi Construct

The design of a $G_q$ (del)/$G_i$ construct was accomplished as follows: the N-tenninal six (6) amino acids (amino acids 2 through 7, having the sequence of TLESIM (SEQ. ID. NO.: 9) of mouse $G\alpha_q$-subunit is deleted and the C-terminal five (5) amino acids, having the sequence EYNLV (SEQ. ID. NO.: 10) was replaced with the corresponding amino acids of the $G_{\alpha}$ i Protein, having the sequence DCGLF (SEQ. ID. NO.: 11).

CXCR3 couples via Gi. The Gq(del)/Gi construct was made as follows: primers were designed as follows This fusion construct is obtained by PCR using the following primers:

(SEQ.ID.NO.:12)
5'-gatcaagcttcCATGGCGTGCTGCCTGAGCGAGGAG-3'
and (SEQ.ID.NO.:13)
5'-gatcggatccTTAGAACAGGCCGCAGTCCTTCAGGTTCAGCTGCAGG ATGGTG-3' and Plasmid 63313 which contained the mouse $G\alpha_q$-wild type version with a hemagglutinin tag as template. Nucleotides in lower caps include cloning sites for HindIII/BamHI and spacers.

TaqPlus Precision DNA polymerase (Stratagene) was utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product was cloned into a pCRII-TOPO vector (nvitrogen) and sequenced using the ABI-Big Dye Terminator kit (P.E. Biosystems). Inserts from a TOPO clone containing the sequence of the fusion construct was shuttled into the expression vector pcDNA3.1(+) at the HindIII/BamHI site by a 2 step cloning process. See, SEQ. ID. NO.:14 for the nucleic acid sequence and SEQ. ID. NO.:15 for the putative amino acid sequence of Gq(del)/Gi construct.

Example 6

Tissue Distribution of the Disclosed Human GPCRs

1. RT-PCR

RT-PCR is applied to confirm the expression and to determine the tissue distribution of human CXCR3. Oligonucleotides utilized are CXCR3-specific and the human multiple tissue cDNA panels (MTC, Clontech) as templates. Taq DNA polymerase (Stratagene) is utilized for the amplification in a 40 µl reaction according to the manufacturer's instructions. 20 µl of the reaction is loaded on a 1.5% agarose gel to analyze the RT-PCR products.

Diseases and disorders related to receptors located in these tissues or regions include, but are not limited to, cardiac disorders and diseases (e.g. thrombosis, myocardial infarction; atherosclerosis; cardiomyopathies); kidney disease/disorders (e.g., renal failure; renal tubular acidosis; renal glycosuria; nephrogenic diabetes insipidus; cystinuria; polycystic kidney disease); eosinopbilia; leukocytosis; leukopenia; ovarian cancer; sexual dysfunction; polycystic ovarian syndrome; pancreatitis and pancreatic cancer; irritable bowel syndrome; colon cancer; Crohn's disease; ulcerative colitis; diverticulitis; Chronic Obstructive Pulmonary Disease (COPD); Cystic Fibrosis; pneumonia; pulmonary hypertension; tuberculosis and lung cancer; Parkinson's disease; movement disorders and ataxias; learning and memory disorders; eating disorders (e.g., anorexia; bulimia, etc.); obesity; cancers; thymoma; myasthenia gravis; circulatory disorders; prostate cancer; prostatitis; kidney disease/disorders (e.g., renal failure; renal tubular acidosis; renal glycosuria; nephrogenic diabetes insipidus; cystinuria; polycystic kidney disease); sensorimotor processing and arousal disorders; obsessive-compulsive disorders; testicular cancer; priapism; prostatitis; hernia; endocrine disorders; sexual dysfunction; allergies; depression; psychotic disorders; migraine; reflux; schizophrenia; ulcers; bronchospasm; epilepsy; prostatic hypertrophy; anxiety; rhinitis; angina; and glaucoma. Accordingly, the methods of the present invention may also be useful in the diagnosis and/or treatment of these and other diseases and disorders.

2. Affymetrix GeneChip® Technology

Sequences from the public database are submitted to Affymetrix for the design and manufacture of microarrays containing oligonucleotides to monitor the expression levels of G protein-coupled receptors (GPCRs) using GeneChip® Technology. RNA samples are amplified, labeled, hybridized to the microarray, and data analyzed according to manufacturer's instructions.

Example 7

Protocol: Direct Identification of Inverse Agonists and Agonists

1. Alpha Screen

The media from Example 3(1) above is aspirated and rinsed 1× with PBS (5-10 ml/flask). 10-20 mls of PBS are added to each flask and let sit for 2-5 minute. The cells are pipetted off into coronal tubes for spinning for 5 minutes at 1500 rpm. PBS is aspirated and re-suspended with Stimulation Buffer (1×HBSS, 0.5 mM IBMX, 5 mM Hepes and 011% BSA). 5 µl/wll of Compound A is diluted in Hepes Buffer and 10 µl/well of cells at 15,000 cells/well will are then added to the wells and incubated for 30 minutes. 5 µl/well of cAMP Acceptor Beads (Perkin Elmer Product No. 6760600R) for a final concentration of 15 µg/ml is added to the wells and then covered and left to incubate for two hours at room temperature. 5 µl of Assay Reaction Mixture is then added. The Assay Reaction Mixture is prepared by mixing the Donor Bead (Perkin Elmer Product No. 6760600R) with a final concentration of 20 µg/ml, Biotinylated cAMP Mix (Perkin Elmer Product No. 6760600R) with a final concentration of 10 nM, and Lysis Buffer (5 mM Hepes and 0.18% Igapel). The wells are covered and incubated for two hours at room temperature. Following incubation, the wells are read on Alpha Quest and measured for light units. The light unit is then converted to pmol cAMP/well by taking the cAMP concentration and determining the pmol/well of cAMP and using the linear regretion function found on GraphPad Prism version 3.00 for Windows, GraphPad Software, San Diego Calif. USA, the light units are converted to pmol cAMP/well.

2. [$^{35}$S]GTPγS Assay

Both endogenous and non-endogenous versions of human CXCR3 can be utilized for the direct identification of candidate compounds as, e.g., inverse agonists. In some embodiments, a GPCR Fusion Protein, as disclosed above, can also be utilized with a non-endogenous, constitutively activated CXCR3. When such a protein is used, intra-assay variation appears to be substantially stabilized, whereby an effective signal-to-noise ratio is obtained. This has the beneficial result of allowing for a more robust identification of candidate compounds. Thus, in some embodiments it is preferred that for direct identification, a CXCR3 Fusion Protein be used and that when utilized, the following assay protocols be utilized.

a. Membrane Preparation

In some embodiments membranes comprising the constitutively active GPCR/Fusion Protein of interest and for use in the direct identification of candidate compounds as inverse agonists or agonists are preferably prepared as follows:

1. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM MgCl$_2$, pH 7.4.

2. Procedure

All materials are kept on ice throughout the procedure. Firstly, the media is aspirated from a confluent monolayer of cells, followed by rinse with 10 ml cold PBS, followed by aspiration. Thereafter, 5 ml of Membrane Scrape Buffer is added to scrape cells; this is followed by transfer of cellular extract into 50 ml centrifuge tubes (centrifuged at 20,000 rpm for 17 minutes at 4° C.). Thereafter, the supernatant is aspirated and the pellet is resuspended in 30 ml Membrane Wash Buffer followed by centrifuge at 20,000 rpm for 17 minutes at 4° C. The supernatant is then aspirated and the pellet resuspended in Binding Buffer. This is homogenized using a Brinkman Polytron™ homogenizer (15-20 second bursts until the all material is in suspension). This is referred to herein as "Membrane Protein".

b. Bradford Protein Assay

Following the homogenization, protein concentration of the membranes is determined using the Bradford Protein Assay (protein can be diluted to about 1.5 mg/ml, aliquoted and frozen (−80° C.) for later use; when frozen, protocol for use is as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

1. Materials

Binding Buffer (as per above); Bradford Dye Reagent; Bradford Protein Standard will be utilized, following manufacturer instructions (Biorad, cat. no. 500-0006).

2. Procedure

Duplicate tubes are prepared, one including the membrane, and one as a control "blank". Each contained 800 µl Binding Buffer. Thereafter, 10 µl of Bradford Protein Standard (1 mg/ml) is added to each tube, and 10 µl of membrane Protein is then added to just one tube (not the blank). Thereafter, 200 µl of Bradford Dye Reagent is added to each tube, followed by vortex of each. After five (5) minutes, the tubes are re-vortexed and the material therein is transferred to cuvettes. The cuvettes are then read using a CECIL 3041 spectrophotometer, at wavelength 595.

c. Direct Identification Assay

1. Materials

GDP Buffer consisted of 37.5 ml Binding Buffer and 2 mg GDP (Sigma, cat. no. G-7127), followed by a series of dilutions in Binding Buffer to obtain 0.2 µM GDP (final concentration of GDP in each well was 0.1 µM GDP); each well comprising a candidate compound, has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 ml Binding Buffer).

2. Procedure

Candidate compounds are preferably screened using a 96-well plate format (these can be frozen at −80° C.). Membrane Protein (or membranes with expression vector excluding the GPCR Fusion Protein, as control), is homogenized briefly until in suspension. Protein concentration is then determined using the Bradford Protein Assay set forth above. Membrane Protein (and control) is diluted to 0.25 mg/ml in Binding Buffer (final assay concentration, 12.5 µg/well). Thereafter, 100 µl GDP Buffer is added to each well of a Wallac Scintistrip™ (Wallac). A 5 ul pin-tool is then used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 μl of Membrane Protein is added to each well (a control well comprising membranes without the GPCR Fusion Protein was also utilized), and pre-incubated for 5-10 minutes at room temperature. Thereafter, 50 μl of [$^{35}$S]GTPγS (0.6 nM) in Binding Buffer is added to each well, followed by incubation on a shaker for 60 minutes at room temperature (again, in this example, plates. were covered with foil). The assay is then stopped by spinning of the plates at 4000 RPM for 15 minutes at 22° C. The plates are then aspirated with an 8 channel manifold and sealed with plate covers. The plates are read on a Wallac 1450 using setting "Prot. #37" (as per manufacturer instructions).

d. Cyclic AMP Assay

Another assay approach to directly identified candidate compound was accomplished by utilizing a cyclase-based assay. In addition to direct identification, this assay approach can be utilized as an independent approach to provide confirmation of the results from the [$^{35}$S]GTPγS approach as set forth above.

A modified Flash Plate™ Adenylyl Cyclase kit (New England Nuclear; Cat. No. SMP004A) is preferably utilized for direct identification of candidate compounds as inverse agonists and agonists to constitutively activated GPCRs in accordance with the following protocol.

Transfected cells are harvested approximately three days after transfection. Membranes are prepared by homogenization of suspended cells in buffer containing 20 mM HEPES, pH 7.4 and 10 mM $MgCl_2$. Homogenization is performed on ice using a Brinkinan Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM $MgCl_2$, to yield a final protein concentration of 0.60 mg/ml (the resuspended membranes are placed on ice until use).

cAMP standards and Detection Buffer (comprising 2 μCi of tracer [$^{125}$I cAMP (100 μl] to 11 ml Detection Buffer) is prepared and maintained in accordance with the manufacturer's instructions. Assay Buffer is prepared fresh for screening and contained 20 mM HEPES, pH 7.4, 10 mM $MgCl_2$, 20 mM phospocreatine (Sigma), 0.1 units/ml creatine phosphokinase (Sigma), 50 μM GTP (Sigma), and 0.2 mM ATP (Sigma); Assay Buffer is then stored on ice until utilized.

Candidate compounds identified as per above (if frozen, thawed at room temperature) are added, preferably, to 96-well plate wells (3 μl/well; 12 μM final assay concentration), together with 40 μl Membrane Protein (30 μg/well) and 50 μl of Assay Buffer. This admixture is then incubated for 30 minutes at room temperature, with gentle shaking.

Following the incubation, 100 μl of Detection Buffer is added to each well, followed by incubation for 2-24 hours. Plates are then counted in a Wallac MicroBeta™ plate reader using "Prot. #31" (as per manufacturer instructions).

Example 8

Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a $G_i$-coupled receptor cause melanosomes to migrate to the center of the cell, resulting in a dramatic lightening in color. If cAMP levels are then raised, following activation of a $G_s$-coupled receptor, the melanosomes are re-dispersed and the cells appear dark again. The increased levels of diacylglycerol that result from activation of $G_q$-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs. Melanophores can be utilized to not only identify compounds against GPCRs, as disclosed below; melanophores can also be used to determine the activity of the receptor.

1. Activity Test

Activity testing allows some degree of quantification of the pigment distribution of the melanophores as a function of the amount of DNA transfected. The test allows optimization of the amount of DNA required and provides an estimate of the expected signal size in a potential screen. Activity tests are performed 48 hrs post-transfection. The cells were removed from the incubator and exposed to room light for one hour. The growth medium on the cells were then replaced with serum-free assay buffer (0.7×L-15) and the cells allowed to equilibrate for a further hour. The cells were then treated with 10 nM Melatonin for 90 minutes to induce full pigment aggregation, followed by 100 nM α-MSH for 60 minutes to produce full pigment dispersion. At each point in this process, the cells were photographed and an absorbance reading measured using a microplate reader. The experiment was aimed at collecting data on the resting, equilibrium state of the melanophores in the assay buffer and to examine the dynamic range of the cells (full pigment aggregation to full pigment dispersion). Both the resting state of the cells and their dynamic range can be affected by the expression of a constitutively active GPCR.

To optimize the dispersion (Gi) signaling activity of non-endogenous constitutively activated CXCR3 ("N134S"), various (20 ug, 50 ug, 75 ug, 100 ug and 200 ug) DNA concentrations were used in the electroporation process. As previously mentioned, activity tests include the numerical as well as visual assessment of the melanophores transfected with CXCR3.

Figure 4:
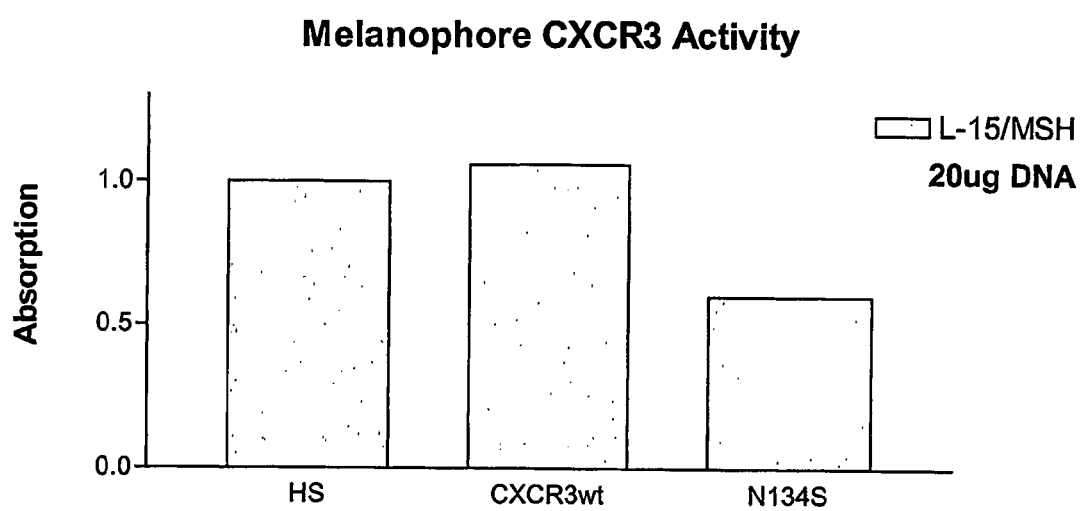
FIG. 4 depicts the L-15/MSH absorptions extracted from tests performed on melanophores transfected with 20 μg DNA of endogenous and non-endogenous CXCR3 plasmid DNA. The L-15/MSH absorbance reading for the cells expressing the non-endogenous constitutively activated version of the CXCR3 ("N134") is significantly lowered because the majority of these cells have aggregated.

In extrapolating the resulting data from varying amounts of DNA, the L-15/MSH ratio shows the level of constitutive signaling to be greater at 20 μg DNA concentrations as compared to mock HS transfected cells. Reference is made to FIG. 4. FIG. 4 evidences the mock-transfected cells (HS) display a normal dynamic range for the melanophores. The L-15/MSH absorbance reading for the cells expressing the non-endogenous constitutively activated version of CXCR3 ("N134S") is significantly lowered because the majority of these cells aggregated. This data evidences that the N134S version is constitutively active.

Melanophores can be utilized to identify compounds, including natural ligands, against GPCRs. This method can be conducted by introducing test cells of a pigment cell line capable of dispersing or aggregating their pigment in response to a specific stimulus and expressing an. exogenous clone coding for the GCPR. Two stimulants can cause pigment aggregation and dispersion. For example, to induce pigment aggregation, the stimulant melatonin can set an initial state of pigment disposition wherein the pigment is aggregated within the test cells if activation of the GPCR induces pigment dispersion. Conversely, to induce pigment dispersion, the stimulant melanocyte stimulating hormone ("MSH") can be used to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods were followed according to the disclosure of U.S. Pat. No. 5,462,856 and U.S. Pat. No. 6,051,386. These patent references are hereby incorporated in their entirety.

2. Functional Activity of CXCR3 with Ligand

Figure 5:
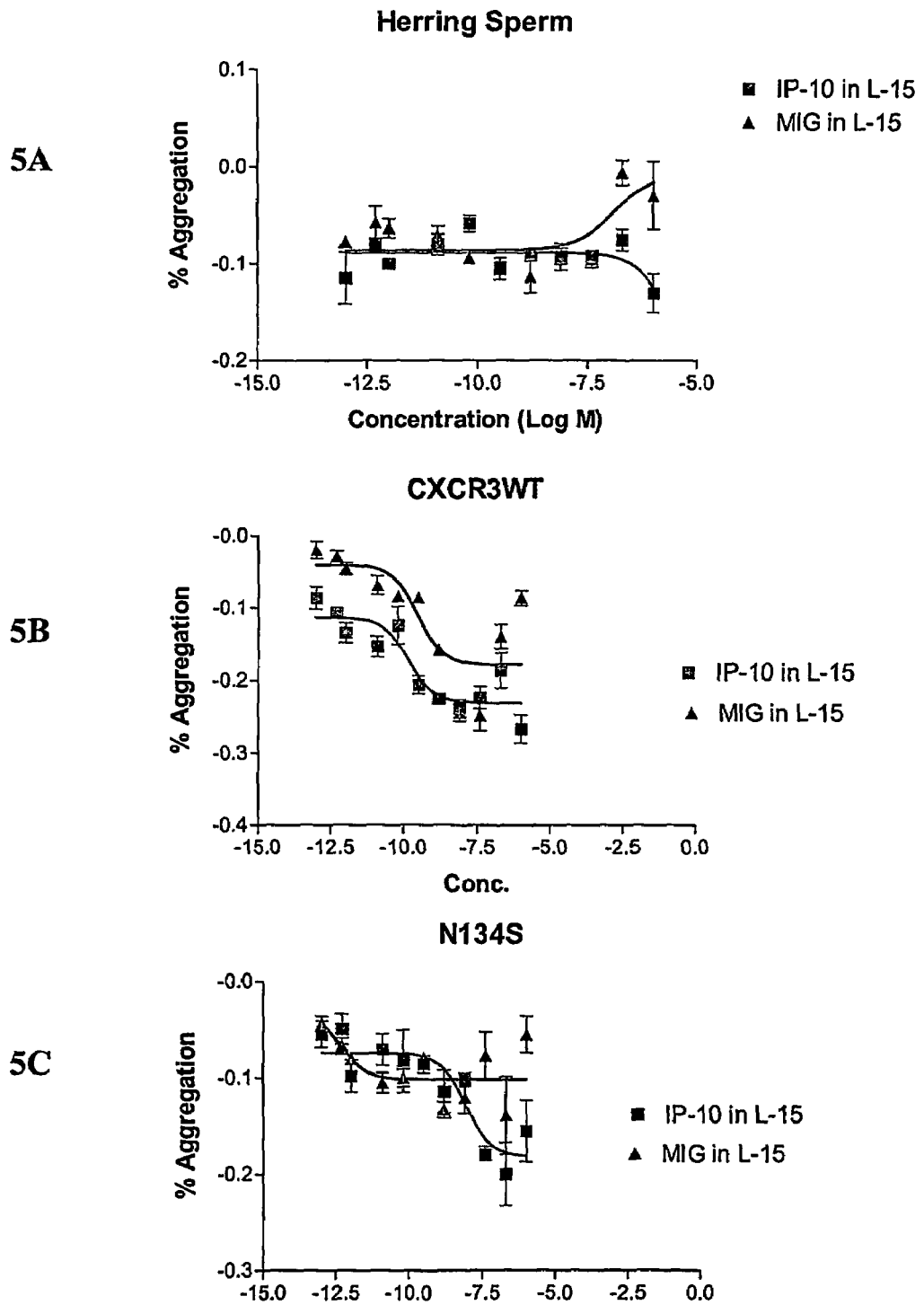
FIGS. 5A-C is a graphic representation of the activation of endogenous CXCR3 ("CXCR3wt") (FIG. 5B) and non-endogenous CXCR3 ("N134S") (FIG. 5C) by viral γ-interferon inducible protein-10 (IP-10) and monokine inducible γ-interferon ("Mig") compared to Herring Sperm (FIG. 5A) as the control. Melanophores were transfected with 25 ug of either CXCR3wt or N134S. The $EC_{50}$ of for IP-10 and Mig were 0.15 nM and 0.29 nM, respectively for the CXCR3wt. The $EC_{50}$ of for IP-10 and Mig were 0.8.3 nM and 0.0.45 nM, respectively for the N134S.

To test the activation as well as functional signaling of CXCR3 in melanophores the following experiment was performed. Melanophores were electroporated as previously described with 50 or 75 ug of endogenous and non-endogenous CXCR3 plasmid DNA. Upon completion of preplating, the melanophore cells were trypsinized and plated at a single density in a poly-D-lysine coated (96 well) plate. Approximately 48 hours post transfection the cells were removed from CFM and placed in 0.7×L-15 for assay. As preliminary experiments suggested that CXCR3 receptor causes melanophore cell aggregation; to view agonist activity on aggregated cells, an aggregation protocol assay was run to further assess this result. Firstly, the cells were placed in 10 nM MSH (0.7×L-15) for approximately 60 minutes prior to treatment. This is routinely done with constitutively activated Gi coupled receptors to get an optimal dynamic range between. aggregation and constitutively activated receptor stimulated aggregation. Specifically, subsequent treatment with IP-10 and Mig after preincubation with MSH shows an evident aggregation response with the agonist for CXCR3, IP-10 and Mig. The results are shown in FIGS. 5A-C. FIG. 5A-C shows a dose dependent response of transfected herring sperm (FIG. 5A), CXCR3 wt (FIG. 5B) and N134S (FIG. 5B) in melanophores to drive aggregation in pre-dispersed cells. The EC50 of for IP-10 and Mig were 0.15 nM and 0.29 nM, respectively for the CXCR3 wt. The EC50 of for IP-10 and Mig were 0.8.3 nM and 0.0.45 nM, respectively for the N134S. Thus the known ligands for CXCR3, IP-10 and Mig, activated the expressed receptor showing Gi coupling as evident in the aggregated state of the cells.

All references cited throughout this patent document, including co-pending and related patent applications are incorporated herein by reference in their entirety. Modifications and extension of the disclosed inventions that are within the purview of the skilled artisan are encompassed within the above disclosure and the claims that follow.

Although a variety of expression vectors are available to those in the art, for purposes of utilization for both the endogenous and non-endogenous human CXCR3, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC#203351.

What is claimed is:

1. A G protein-coupled receptor (GPCR) comprising an amino acid sequence that is that is at least 80% identical to SEQ ID NO:6, wherein said GPCR is constitutively active and has an amino acid residue other than asparagine at an amino acid position corresponding to amino acid position 134 of SEQ ID NO:6.

2. The GPCR of claim 1, wherein the amino acid other than asparagine is serine.

3. The GPCR of claim 1, wherein said G protein-coupled receptor comprises the amino acid sequence set forth in SEQ ID NO:6.

4. A fusion protein comprising a G protein and a GPCR of claim 1.

5. A polynucleotide encoding a G protein-coupled receptor (GPCR) comprising an amino acid sequence that is that is at least 80% identical to SEQ ID NO:6, wherein said GPCR is constitutively active and has an amino acid residue other than asparagine at an amino acid position corresponding to amino acid position 134 of SEQ ID NO:6.

6. A vector comprising a polynucleotide encoding a G protein-coupled receptor (GPCR) comprising an amino acid sequence that is that is at least 80% identical to SEQ ID NO:6, wherein said GPCR is constitutively active and has an amino acid residue other than asparagine at an amino acid position corresponding to amino acid position 134 of SEQ ID NO:6.

7. The vector of claim 6, wherein said vector is an expression vector, and said polynucleotide is operably linked to a promoter.

8. A recombinant host cell comprising a polynucleotide encoding a G protein-coupled receptor (GPCR) comprising an amino acid sequence that is that is at least 80% identical to SEQ ID NO:6, wherein said GPCR is constitutively active and has an amino acid residue other than asparagine at an amino acid position corresponding to amino acid position 134 of SEQ ID NO:6.

9. A method of producing a protein comprising:
culturing a host cell comprising a polynucleotide encoding a G protein-coupled receptor (GPCR) comprising an amino acid sequence that is that is at least 80% identical to SEQ ID NO:6, wherein said GPCR is constitutively active and has an amino acid residue other than asparagine at an amino acid position corresponding to amino acid position 134 of SEQ ID NO:6.

10. The method of claim 9, further comprising isolating a membrane from said host cell, wherein said membrane comprises said GPCR.

11. A method of screening comprising:
(a) contacting a candidate compound with a G protein-coupled receptor (GPCR) comprising an amino acid sequence that is that is at least 80% identical to SEQ ID NO:6, wherein said GPCR is constitutively active and has an amino acid residue other than asparagine at an amino acid position corresponding to amino acid position 134 of SEQ ID NO:6; and
(b) determining whether the candidate compound inhibits or stimulates said receptor.

12. The method of claim 11, wherein the amino acid other than asparagine is serine.

13. The method of claim 11, wherein the GPCR comprises the amino acid sequence set forth in SEQ ID NO:6.

14. The method of claim 11, wherein said GPCR is part of a fusion protein that further contains a G protein.

15. The method of claim 11, wherein the method comprises determining whether said candidate compound is an inverse agonist, agonist, partial agonist or antagonist of said GPCR.

16. The method of claim 11, wherein the method comprises determining whether said candidate compound is an inverse agonist of the receptor.

17. The method of claim 15, wherein the method further comprises formulating said inverse agonist, agonist, partial agonist or antagonist as a pharmaceutical.

18. The method of claim 16, wherein the method further comprises formulating said inverse agonist as a pharmaceutical.

19. The method of claim 11, wherein said GPCR is present on a host cell or an isolated membrane thereof.

20. The method of claim 19, wherein the host cell is a mammalian host cell.

21. The method of claim 19, wherein the host cell is a melanophore host cell.

* * * * *

UNITED STATES PATENT AND TRADEMARK OFFICE
CERTIFICATE OF CORRECTION

PATENT NO. : 7,427,487 B2  Page 1 of 1
APPLICATION NO. : 10/548898
DATED : September 23, 2008
INVENTOR(S) : Villegas et al.

It is certified that error appears in the above-identified patent and that said Letters Patent is hereby corrected as shown below:

In Column 45, Claim 9, line 26, following "SEQ ID NO:6", insert the following text:

-- under conditions which allow expression of said GPCR. --

Signed and Sealed this

Twenty-third Day of December, 2008

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 1107
<212> TYPE: DNA
<213> ORGANISM: Homo sapien

<400> SEQUENCE: 1
atggtccttg aggtgagtga ccaccaagtg ctaaatgacg ccgaggttgc cgccctcctg       60
gagaacttca gctcttccta tgactatgga gaaaacgaga gtgactcgtg ctgtacctcc      120
ccgccctgcc cacaggactt cagcctgaac ttcgaccggg ccttcctgcc agccctctac     180
agcctcctct ttctgctggg gctgctgggc aacggcgcgg tggcagccgt gctgctgagc     240
cggcggacag ccctgagcag caccgacacc ttcctgctcc acctagctgt agcagacacg      300
ctgctggtgc tgacactgcc gctctgggca gtggacgctg ccgtccagtg ggtctttggc     360
tctggcctct gcaaagtggc aggtgccctc ttcaacatca acttctacgc aggagccctc      420
ctgctggcct gcatcagctt tgaccgctac ctgaacatag ttcatgccac ccagctctac     480
```

```
cgccggggc  ccccggcccg  cgtgaccctc  acctgcctgg  ctgtctgggg  gctctgcctg   540
cttttcgccc  tcccagactt  catcttcctg  tcggcccacc  acgacgagcg  cctcaacgcc   600
acccactgcc  aatacaactt  cccacaggtg  ggccgcacgg  ctctgcgggt  gctgcagctg   660
gtggctggct  ttctgctgcc  cctgctggtc  atggcctact  gctatgccca  catcctggcc   720
gtgctgctgg  tttccagggg  ccagcggcgc  ctgcgggcca  tgcggctggt  ggtggtggtc   780
gtggtggcct  tgccctctg   ctggaccccc  tatcacctgg  tggtgctggt  ggacatcctc   840
atggacctgg  gcgctttggc  ccgcaactgt  ggccgagaaa  gcagggtaga  cgtggccaag   900
tcggtcacct  caggcctggg  ctacatgcac  tgctgcctca  acccgctgct  ctatgccttt   960 gtagggtca   agttccggga  gcggatgtgg  atgctgctct  tgcgcctggg  ctgccccaac  1020
cagagagggc  tccagaggca  gccatcgtct  tcccgccggg  attcatcctg  gtctgagacc  1080
tcagaggcct  cctactcggg  cttgtga                                         1107
```

<210> SEQ ID NO 2
<211> LENGTH: 368
<212> TYPE: PRT
<213> ORGANISM: Homo sapien

<400> SEQUENCE: 2

```
Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Val Ala Phe Ala Leu Cys Trp Thr Pro Tyr His
```

```
                260                 265                 270
Leu Val Val Val Asp Ile Leu Met Asp Leu Gly Ala Leu Ala Arg
        275                 280                 285
Asn Cys Gly Arg Glu Ser Arg Val Asp Val Ala Lys Ser Val Thr Ser
        290                 295                 300
Gly Leu Gly Tyr Met His Cys Cys Leu Asn Pro Leu Leu Tyr Ala Phe
305                 310                 315                 320
Val Gly Val Lys Phe Arg Glu Arg Met Trp Met Leu Leu Leu Arg Leu
                325                 330                 335
Gly Cys Pro Asn Gln Arg Gly Leu Gln Arg Gln Pro Ser Ser Ser Arg
        340                 345                 350
Arg Asp Ser Ser Trp Ser Glu Thr Ser Glu Ala Ser Tyr Ser Gly Leu
        355                 360                 365

<210> SEQ ID NO 3
<211> LENGTH: 48
<212> TYPE: DNA
<213> ORGANISM: Artificial
<220> FEATURE:
<223> OTHER INFORMATION: Primer Sequence

<400> SEQUENCE: 3
acgaattcag ccatggtcct tgaggtgagt gaccaccaag tgctaaat          48

<210> SEQ ID NO 4
<211> LENGTH: 27
<212> TYPE: DNA
<213> ORGANISM: Artificial
<220> FEATURE:
<223> OTHER INFORMATION: Primer Sequence

<400> SEQUENCE: 4
gaggatcctg gaatgcgggg aagtcag                                27

<210> SEQ ID NO 5
<211> LENGTH: 1107
<212> TYPE: DNA
<213> ORGANISM: Artificial
<220> FEATURE:
<223> OTHER INFORMATION: Novel Sequence

<400> SEQUENCE: 5
atggtccttg aggtgagtga ccaccaagtg ctaaatgacg ccgaggttgc cgccctcctg      60
gagaacttca gctcttccta tgactatgga gaaaacgaga gtgactcgtg ctgtaccctc     120
ccgccctgcc acaggacttc agcctgaac ttcgaccggg ccttcctgcc agccctctac     180
agcctcctct ttctgctggg gctgctgggc aacggcgcgg tggcagccgt gctgctgagc     240
cggcggacag ccctgagcag caccgacacc ttcctgctcc acctagctgt agcagacacg     300
ctgctggtgc tgacactgcc gctctgggca gtggacgctg ccgtccagtg ggtctttggc     360
tctggcctct gcaaagtggc aggtgccctc ttcaacatca gcttctacgc aggagccctc     420
ctgctggcct gcatcagctt tgaccgctac ctgaacatag ttcatgccac ccagctctac     480
cgccggggc ccccggcccg cgtgaccctc acctgcctgg ctgtctgggg gctctgcctg     540
cttttcgccc tccagacttc atcttcctg tcggcccacc acgacgagcg cctcaacgcc     600
acccactgcc aatacaactt cccacaggtg ggccgcacgg ctctgcgggt gctgcagctg     660
gtggctggct ttctgctgcc cctgctggtc atggcctact gctatgccca catcctggcc     720
gtgctgctgg tttccagggg ccagcggcgc ctgcgggcca tgcggctggt ggtggtggtc     780
```

```
gtggtggcct ttgccctctg ctggacccccc tatcacctgg tggtgctggt ggacatcctc    840
atggacctgg gcgctttggc ccgcaactgt ggccgagaaa gcagggtaga cgtggccaag    900
tcggtcacct caggcctggg ctacatgcac tgctgcctca acccgctgct ctatgccttt    960
gtaggggtca agttccggga gcggatgtgg atgctgctct tgcgcctggg ctgccccaac   1020
cagagagggc tccagaggca gccatcgtct ccccgccggg attcatcctg gtctgagacc   1080
tcagaggcct cctactcggg cttgtga                                       1107
```

<210> SEQ ID NO 6
<211> LENGTH: 368
<212> TYPE: PRT
<213> ORGANISM: Artificial
<220> FEATURE:
<223> OTHER INFORMATION: Novel Sequence

<400> SEQUENCE: 6

```
Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Gly Asn Gly Ala Val Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Ser Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
    290                 295                 300
```

```
Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
                340                 345                 350

Arg Asp Ser Ser Trp Ser Glu Thr Ser Glu Ala Ser Tyr Ser Gly Leu
        355                 360                 365
```

<210> SEQ ID NO 7
<211> LENGTH: 31
<212> TYPE: DNA
<213> ORGANISM: Artificial
<220> FEATURE:
<223> OTHER INFORMATION: Primer Sequence

<400> SEQUENCE: 7
ccctcttcaa catcagcttc tacgcaggag c                                    31

<210> SEQ ID NO 8
<211> LENGTH: 31
<212> TYPE: DNA
<213> ORGANISM: Artificial
<220> FEATURE:
<223> OTHER INFORMATION: Primer Sequence

<400> SEQUENCE: 8
gctcctgcgt agaagctgat gttgaagagg g                                    31

<210> SEQ ID NO 9
<211> LENGTH: 6
<212> TYPE: PRT
<213> ORGANISM: Artificial
<220> FEATURE:
<223> OTHER INFORMATION: Novel Sequence

<400> SEQUENCE: 9

```
Thr Leu Glu Ser Ile Met
1               5
```

<210> SEQ ID NO 10
<211> LENGTH: 5
<212> TYPE: PRT
<213> ORGANISM: Artificial
<220> FEATURE:
<223> OTHER INFORMATION: Novel Sequence

<400> SEQUENCE: 10

```
Glu Tyr Asn Leu Val
1               5
```

<210> SEQ ID NO 11
<211> LENGTH: 5
<212> TYPE: PRT
<213> ORGANISM: Artificial
<220> FEATURE:
<223> OTHER INFORMATION: Novel Sequence

<400> SEQUENCE: 11

```
Asp Cys Gly Leu Phe
1               5
```

<210> SEQ ID NO 12
<211> LENGTH: 36

-continued

<212> TYPE: DNA
<213> ORGANISM: Artificial
<220> FEATURE:
<223> OTHER INFORMATION: Primer Sequence

<400> SEQUENCE: 12
gatcaagctt ccatggcgtg ctgcctgagc gaggag                          36

<210> SEQ ID NO 13
<211> LENGTH: 53
<212> TYPE: DNA
<213> ORGANISM: Artificial
<220> FEATURE:
<223> OTHER INFORMATION: Primer Sequence

<400> SEQUENCE: 13
gatcggatcc ttagaacagg ccgcagtcct tcaggttcag ctgcaggatg gtg       53

<210> SEQ ID NO 14
<211> LENGTH: 1062
<212> TYPE: DNA
<213> ORGANISM: Artificial
<220> FEATURE:
<223> OTHER INFORMATION: Novel Sequence

<400> SEQUENCE: 14
atggcgtgct gcctgagcga ggaggccaag gaagcccgga ggatcaacga cgagatcgag    60
cggcagctgc gcagggacaa cgcgacgcc cgccgggagc tcaagctgct gctgctgggg    120
acaggggaga gtggcaagtc gaccttcatc aagcagatga ggatcatcca cgggtcgggc    180
tactctgacg aagacaagcg cggcttcacc aagctggtgt atcagaacat cttcacggcc    240
atgcaggcca tgatcagagc gatggacaca ctcaagatcc catacaagta tgaacacaat    300
aaggctcatg cacaattggt tcgagaggtt gatgtggaga aggtgtctgc ttttgacgtc    360
cccgactacg cggcaataaa gagcttgtgg aatgatcctg aatccaggga gtgctacgac    420
agacgacggg aatatcagtt atctgactct accaaatact atctgaatga cttggaccgt    480
gtagccgacc cttcctatct gcctacacaa caagacgtgc ttagagttcg agtccccact    540
acagggatca tcgaataccc ctttgactta caaagtgtca ttttcagaat ggtcgatgta    600
gggggccaaa ggtcagagag aagaaaatgg atccactgct ttgaaaatgt cacctccatc    660
atgtttctag tagcgcttag cgaatatgat caagttcttg tggagtcaga caatgagaac    720
cgcatggagg agagcaaagc actctttaga acaattatca cctaccccctg gttccagaac    780 tcctctgtga ttctgttctt aaacaagaaa gatcttctag aggagaaaat catgtattcc    840
cacctagtcg actacttccc agaatatgat ggacccagaa gagatgccca ggcagctcga    900
gaattcatcc tgaaaatgtt cgtggacctg aaccccgaca gtgacaaaat catctactcc    960
cacttcacgt gcgccacaga taccgagaac atccgcttcg tctttgcagc cgtcaaggac    1020
accatcctgc agctgaacct gaaggactgc ggcctgttct aa                      1062

<210> SEQ ID NO 15
<211> LENGTH: 353
<212> TYPE: PRT
<213> ORGANISM: Artificial
<220> FEATURE:
<223> OTHER INFORMATION: Novel Sequence

<400> SEQUENCE: 15

Met Ala Cys Cys Leu Ser Glu Glu Ala Lys Glu Ala Arg Arg Ile Asn
1               5                   10                  15

-continued

```
Asp Glu Ile Glu Arg Gln Leu Arg Arg Asp Lys Arg Asp Ala Arg Arg
         20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Ser Gly Tyr Ser Asp Glu
         50                  55                  60

Asp Lys Arg Gly Phe Thr Lys Leu Val Tyr Gln Asn Ile Phe Thr Ala
65                       70                  75                  80

Met Gln Ala Met Ile Arg Ala Met Asp Thr Leu Lys Ile Pro Tyr Lys
                 85                  90                  95

Tyr Glu His Asn Lys Ala His Ala Gln Leu Val Arg Glu Val Asp Val
                 100                 105                 110

Glu Lys Val Ser Ala Phe Asp Val Pro Asp Tyr Ala Ala Ile Lys Ser
                 115                 120                 125

Leu Trp Asn Asp Pro Gly Ile Gln Glu Cys Tyr Asp Arg Arg Arg Glu
         130                 135                 140

Tyr Gln Leu Ser Asp Ser Thr Lys Tyr Tyr Leu Asn Asp Leu Asp Arg
145                      150                 155                 160

Val Ala Asp Pro Ser Tyr Leu Pro Thr Gln Gln Asp Val Leu Arg Val
                 165                 170                 175

Arg Val Pro Thr Thr Gly Ile Ile Glu Tyr Pro Phe Asp Leu Gln Ser
                 180                 185                 190

Val Ile Phe Arg Met Val Asp Val Gly Gly Gln Arg Ser Glu Arg Arg
                 195                 200                 205

Lys Trp Ile His Cys Phe Glu Asn Val Thr Ser Ile Met Phe Leu Val
         210                 215                 220

Ala Leu Ser Glu Tyr Asp Gln Val Leu Val Glu Ser Asp Asn Glu Asn
225                      230                 235                 240

Arg Met Glu Glu Ser Lys Ala Leu Phe Arg Thr Ile Ile Thr Tyr Pro
                 245                 250                 255

Trp Phe Gln Asn Ser Ser Val Ile Leu Phe Leu Asn Lys Lys Asp Leu
                 260                 265                 270

Leu Glu Glu Lys Ile Met Tyr Ser His Leu Val Asp Tyr Phe Pro Glu
         275                 280                 285

Tyr Asp Gly Pro Gln Arg Asp Ala Gln Ala Ala Arg Glu Phe Ile Leu
         290                 295                 300

Lys Met Phe Val Asp Leu Asn Pro Asp Ser Asp Lys Ile Ile Tyr Ser
305                      310                 315                 320

His Phe Thr Cys Ala Thr Asp Thr Glu Asn Ile Arg Phe Val Phe Ala
                 325                 330                 335

Ala Val Lys Asp Thr Ile Leu Gln Leu Asn Leu Lys Asp Cys Gly Leu
                 340                 345                 350

Phe
```